US012636241B1

(12) United States Patent
Vohra et al.

(10) Patent No.: US 12,636,241 B1
(45) Date of Patent: May 26, 2026

(54) METHOD AND COMPOSITION FOR OXIDATIVE HAIR COLORING

(71) Applicant: Wella Operations US LLC, Calabasas, CA (US)

(72) Inventors: Firoj Vohra, Hackettstown, NJ (US); Graham Neil Mckelvey, Glashütten (DE)

(73) Assignee: Wella Operations US LLC, Calabasas, CA (US)

( * ) Notice: Subject to any disclaimer, the term of this patent is extended or adjusted under 35 U.S.C. 154(b) by 0 days.

(21) Appl. No.: 19/041,454

(22) Filed: Jan. 30, 2025

(51) Int. Cl.

| | |
|---|---|
| ***A61K 8/41*** | (2006.01) |
| ***A61K 8/19*** | (2006.01) |
| ***A61K 8/44*** | (2006.01) |
| ***A61K 8/49*** | (2006.01) |
| ***A61Q 5/10*** | (2006.01) |

(52) U.S. Cl.

CPC ................ *A61K 8/411* (2013.01); *A61K 8/19* (2013.01); *A61K 8/415* (2013.01); *A61K 8/44* (2013.01); *A61K 8/498* (2013.01); *A61Q 5/10* (2013.01); *A61K 2800/30* (2013.01); *A61K 2800/42* (2013.01); *A61K 2800/882* (2013.01)

(58) Field of Classification Search

CPC .................................. A61K 8/41; A61Q 5/10
USPC .......................................................... 8/405
IPC ..................................................... A61K 8/411
See application file for complete search history.

(56) References Cited

U.S. PATENT DOCUMENTS

| | | | | |
|---|---|---|---|---|
| 7,481,846 B2 * | 1/2009 | Marsh | A61K 8/22 8/405 |
| 2021/0177717 A1 * | 6/2021 | Consoli | A61K 8/19 |

* cited by examiner

*Primary Examiner* — Walter E Webb

(74) *Attorney, Agent, or Firm* — Dennemeyer & Associates LLC

(57) ABSTRACT

The present invention is directed to embodiments of a method for coloring hair using an oxidative hair coloring composition based upon the primary dye compounds MBB, Aminol and optional secondary precursor and coupler compounds PAP, DPE, MAP, AHT and EOAP, a carbonate and/or bicarbonate source, an alkalizer and one or more amino acids. Additional subsidiary precursors and couplers may be included to broaden the color space delivered by the primary dye compounds. The oxidative hair coloring composition is free of resorcinol and C1-C10 alkyl resorcinol. The L*a*b* color space of embodiments of the oxidative hair coloring composition as measured by L*a*b* techniques is about the same as that delivered by the resorcinol based composition.

17 Claims, No Drawings

METHOD AND COMPOSITION FOR OXIDATIVE HAIR COLORING

FIELD OF THE INVENTION

The invention is directed to a method and composition for coloring of hair. The oxidative hair coloring composition and corresponding method are based upon a combination of one or more couplers and one or more precursors and an L* ingredient mixture. The composition and method deliver pseudo-resorcinol control of L* negative progression of the color space for the treated hair, roots to tips and display a broad color space like that typically delivered by a resorcinol based hair coloring composition. The composition excludes resorcinol and any of its alkyl or halogen derivatives.

BACKGROUND OF THE INVENTION

The hair coloring technique utilizing permanent oxidative color compositions is well-known in the art. These coloring products have been used in professional salons and in retail products for use at home for decades. Coloring products typically comprise a tint composition and an oxidizing composition which are packaged separately and mixed immediately before use to form the coloring composition. The tint composition typically contains one or more dye precursors, one or more couplers and an alkalizing agent, usually ammonia or an amine such as mono-ethanol amine. The dye precursors react with the couplers in the presence of an oxidizing agent to form larger, colored products within the hair. The oxidizing agent, typically hydrogen peroxide, enables the coloring process through its oxidation of the dye precursors which react with the couplers to form the large colored products. The hydrogen peroxide, especially in the presence of an alkalizing agent, also bleaches the natural melanin of the hair, so that the original hair color is minimized or eliminated and new shades of hair color lighter or darker than the original shade can be produced. This process is described for example in the European Scientific Committee on Consumer Products Opinion 1198/08, January 2009.

According to the state of the art, creation of a large variety of different shades generally involves a combination of different couplers and dye precursors. Traditionally, the couplers have been based upon resorcinol and its closely related alkyl derivatives. These couplers have been able to produce rich color spaces spanning the visible color spectrum when combined with selected variations of the dye precursors.

The color development of a typical batch of resorcinol oxidative dye covers a rich CIELAB spectrum and employs high concentrations of precursor and the coupler resorcinol. The rate of production optimized by use of high pH, 10 or 11. At this pH level, however, hydrogen peroxide can cause significant damage to the hair. An attempt to lessen this hair strand damage is described in U.S. Pat. No. 7,481,846. The '846 patent indicates that addition of a source of peroxymonocarbonate to resorcinol oxidative dyes provides better oxidation efficiency around pH 9, thereby lowering the harsh pH effect on hair strands. However, the '846 patent states that the percarbonate/perbicarbonate oxidizer has its own hair damage problem so that '846 adds a radical scavenger to counteract the perbicarbonate hair damage.

Irrespective of pH and kind of oxidation agent used, the resorcinol oxidative dye production continues rapidly until the precursor, resorcinol and hydrogen peroxide concentrations become exhausted. The corresponding degree of color production progresses along the L*axis of the CIELAB color spectrum for a short period of time and then essentially does not progress further. This developmental aspect delivers a ready, easy, manipulatable ability so that the color development for succeeding swatches of hair will be substantially to essentially uniform.

Recent safety, health and environmental issues have been raised with respect to the use of resorcinol. Questions regarding allergic reactions, untoward endocrine disrupting properties, sensitizing potency and long term toxic and cellular alteration effects have been raised with the effect that governmental regulatory agencies have begun considering a ban on the use of the resorcinol coupler. To this end, in January 2022, the European Commission Scientific Committee on Consumer Safety decreed that resorcinol constitutes a substance of very high concern (SVHC) meaning it is not to be incorporated in oxidative hair dye compositions in Europe.

This EC directive has motivated cosmetic companies to develop alternatives to resorcinol based oxidative hair dyes. Unfortunately, non-resorcinol oxidative hair dyes have been unable to achieve the rich color space results produced by resorcinol based oxidative hair dyes. Moreover, non-resorcinol based oxidative hair compositions have been unable to manage root to tip coverage and provide an even appearance similar to those produced by resorcinol based compositions. Additionally, these non-resorcinol compositions continue to develop color in the CIELAB L* color space (continue to darken) for long periods of time so that a first portion of hair colored in this manner continues to darken until it and the last portion of colored hair are rinsed to stop coloring action. This unfortunate result typically produces unevenly colored hair.

There is consequently a need for the development of hair coloring methods and hair coloring compositions that do not utilize resorcinol, deliver color space spectra similar to those of resorcinol based compositions and enable at least substantially uniform root to tip coverage. A further need is to provide methods and compositions using coupler replacements that are regarded as having lower and/or no concerns in regard to safety, environmental, health and toxicity issues. At the same time there is a need to provide methods and hair coloring compositions that mimic the rich color spaces over the entire visible light spectrum provided by the resorcinol oxidative hair dye technology and stop the coloring action after a short period of time.

SUMMARY OF THE INVENTION

These and other needs are achieved by the present invention which is directed to an inventively designed oxidative coloration technology. The oxidative coloration technology is free of resorcinol and its alkyl and halogen derivatives yet provides a visible color space substantially to essentially similar to that produced by resorcinol hair coloring compositions. Moreover, this oxidative coloration technology which is free of resorcinol and its derivatives has been found to control the CIELAB L*a*b* color development progression through its pseudo-resorcinol control property.

The first aspect of this technology includes embodiments of a method for applying to hair an oxidative hair coloring composition. A second aspect of this technology includes embodiments of the oxidative hair coloring composition itself. These embodiments are free of resorcinol, its C1-C10 alkyl derivatives and its halogen derivatives.

Embodiments of the oxidative hair coloring composition comprise a combination of a tint composition comprising at least one primary precursor, at least one primary coupler and an L* mixture, as well as an oxidizer composition comprising at least hydrogen peroxide.

Embodiments of the method comprise treating hair, preferably human hair of a person, with embodiments of the oxidative hair coloring composition, allowing embodiments of the composition to remain on the hair for a time at least as long as the color development period and then, at leisure at any time, rinsing. A further aspect of embodiments of a method includes forming the oxidative hair coloring composition from the kit described below and applying the oxidative hair coloring composition to the hair.

An additional aspect of this technology includes embodiments of a kit for practice of the method. The separate kit components comprise a) the oxidizer composition and b) the tint composition including at least one primary precursor, at least one primary coupler and the L* mixture.

The pseudo-resorcinol control property of these embodiments of the method and composition means that the L* value of the CIELAB color space of developing color progression of these embodiments mimics the resorcinol L* control of the progress of color development of a corresponding oxidative hair dye composition containing resorcinol so that progress in the negative direction along the L* axis of the CIELAB color space is managed so as to reach substantially a constant level during a period of from about 20 to about 30 minutes.

Embodiments of the oxidative hair coloring composition for use to treat hair according to embodiments of the method comprise at least the primary ingredients A, B and C:

1) precursor A comprising 2-methoxymethyl-p-phenylene diamine (MBB), its addition salts, its solvates and/or solvates of its salts;
2) coupler B comprising hydroxyethyl-3,4-methylenedioxyaniline (Aminol), its addition salts, it solvates and/or solvates of its salts, and,
3) an L* mixture C comprising a carbonate and/or bicarbonate source, one or more amino acids and a source of ammonium cation.

Embodiments of the oxidative hair coloring composition contain no resorcinol, nor any C1-C10 alkyl resorcinol, nor any halogen resorcinol. Embodiments of the oxidative hair coloring composition have the pseudo-resorcinol L* control property that mimics the effect resorcinol has upon the L* value progression of the CIELAB color space of the developing color of a corresponding oxidative hair dye composition that contains resorcinol. The pseudo-resorcinol property enables easy coloring without concern for continued L* darkening.

Embodiments of the oxidative hair coloring composition additionally can comprise secondary precursor and/or coupler ingredients including but not limited to the following secondary precursor (a) and secondary couplers (b-e).

a. p-aminophenol (PAP), its addition salts, its solvates and/or solvates of its salts;
b. 2,4-diaminophenoxyethanol (DPE), its addition salts, its solvates and/or solvates of its salts;
c. m-aminophenol (MAP), its addition salts, its solvates and/or solvates of its salts; and
d. 4-amino-2-hydroxy toluene (AHT), its addition salts, its solvates and/or solvates of its salts; and,
e. ethyl ortho-amino phenol (EOAP), its addition salts, its solvates and/or solvates of its salts.

Embodiments of the oxidative hair coloring composition additionally can comprise combinations of subsidiary precursors and subsidiary couplers: i) with the primary ingredients A, B and C alone, or ii) with these primary ingredients and one or more of the secondary precursor and/or coupler ingredients. The subsidiary couplers and precursors are described in the Detailed Description.

A second aspect of this technology concerns embodiments of the oxidizer composition component which together with embodiments of the tint composition comprise embodiments of the oxidative hair coloring composition for practice of embodiments of the method. Embodiments of the oxidizer composition for development of the oxidative hair coloring composition comprise at least hydrogen peroxide. The L* mixture C of embodiments of the tint composition component combines with the hydrogen peroxide to produce an oxidizing salt, the anion peroxycarbonate and/or peroxybicarbonate as well as an amino acid salt when the tint composition and oxidizer composition components are combined. The combination of peroxycarbonate and/or peroxybicarbonate and the amino acid salt provides the pseudo-resorcinol control of the color development of the oxidative hair coloring composition.

A third aspect of this technology concerns embodiments of the chassis to be included with the tint composition component and with the oxidative hair coloring composition for practice of embodiments of the method. Embodiments of this chassis enable delivery of substantially uniform root to tip coverage. Embodiments of the chassis comprise two kinds of surfactant: a phosphate ester/acid surfactant/fatty alcohol combination and a nonionic surfactant with viscosity control agent and no fatty acid or fatty ester.

Another aspect of the invention concerns embodiments of a kit of the components that can be combined to form the oxidative hair coloring composition described above. Embodiments of the kit comprise the two separate components: the tint composition and the oxidizer composition.

A further aspect of the invention concerns embodiments of a method for coloring hair using the above-described kit. The tint composition and the oxidizer composition components of the kit are combined to form embodiments of the oxidative hair coloring composition at basic pH immediately before application to the hair according to the method. According to embodiments of the method, embodiments of the resulting oxidative hair coloring composition are applied to the hair and allowed to remain on the hair for a time at least as long as the pseudo-resorcinol control of the color development period of the oxidative hair coloring composition. Following this treatment period, the hair may be rinsed at leisure with water to remove residue and excess portions of the oxidative hair coloring composition.

The method for coloring hair with the oxidative hair coloring composition produced by combining the tint and oxidizer composition components of the kit produces hair having a tone and hue showing a visible color space spectrum throughout roots and tips as defined by the combination of various precursors and couplers including but not limited to the primary precursor MBB and the primary coupler Aminol. If a combination of the above-described secondary precursors and couplers is included, the visible color space spectrum of the colors produced on hair delivers a brown to light brown tone and hue as demonstrated by the examples below. Use of subsidiary precursor and coupler mixtures described below deliver other visible color space spectra and provide a tint of the hair from light brown to auburn to rust/reddish to blond. Of course, primary colors unlike natural hair color can also be produced such as green, yellow, blue, red, orange and purple tints.

Definitions

Unless defined otherwise, all technical and scientific terms used herein have the same meaning as commonly understood by a person of ordinary skill in the art.

As used in the specification and the appended statements, the singular forms "a," "an" and "the" include plural referents unless the context clearly dictates otherwise. Also use of a plural term describing a thing or element includes the singular unless the context clearly dictates otherwise. For example, the terms fatty alcohols or hydrocarbons include a single fatty alcohol or a single hydrocarbon as well as multiples.

The term "may" in the context of this application means "is able to" and is a synonym for the term "can" and is a "helper" syntax term with "is/be", "includes" and "comprises." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The term "about" is understood to mean±10 percent of the recited number, numbers or range of numbers.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format are to be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" are to be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

The terms "comprising", "comprises" and "comprised of" as used herein are synonymous with "including", "includes" or "containing", "contains", and are inclusive or open-ended and do not exclude additional, non-recited members, elements or method steps.

The term "anagenic hair" as used herein means hair strands that are in direct connection with a hair follicle which is in either the anagen or telogen state. Anagenic hair is present in one of these states on a scalp of a person, a human, and its follicle is appurtenant to a sebum gland that substantially continuously secretes sebum and long chain fatty acids onto the surfaces of the hair shaft. As the hair grows from the follicle, it carries with it coatings of secreted sebum and long chain fatty acids. The fatty acid coating is known as the f layer and is tightly entwined with the keratin protein at the hair shaft surface. Hair cut from a person is no longer anagenic hair.

Keratin fibers means hair strands on the scalp of a person, preferably anagenic hair. Keratin fibers, aka hair strands, are comprised of cells forming an inner cortex as the core and a cuticle as the outer covering surrounding the cuticle. The hair strand chemical components include proteins, polynucleic acids, amino acids, minerals, melanin, lipids including fatty acids, fatty alcohols, triglycerides, phospholipids, cholesterol, and squalene. These components are configured as cells, fibrils, connective tissue, extracellular links, pigments, keratin and associated structures. The outer layer of the cuticle is configured as a sheath of overlapping flat cells having a structure like the bark of a palm tree or scales of a fish. Like the scales of a fish, the surface of the cuticle is smooth in the direction from the root to the tip and rough in the direction from the tip to the root.

In the following passages, different aspects of the subject matter are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "preferred embodiment" means that a particular feature, structure, or characteristic described in connection with the embodiment is included in at least one embodiment of the presently claimed invention. Thus, appearances of the phrases "in one embodiment" or "in a preferred embodiment" in various places throughout this specification are not necessarily all referring to the same embodiment but may refer to different embodiments of the presently claimed invention. Furthermore, the features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the subject matter, and form different embodiments, as would be understood by those in the art. For example, in the appended claims, any of the claimed embodiments can be used in any combination.

For the purposes of the presently claimed invention, '% by weight' or 'wt %' as used in the presently claimed invention is with respect to the total weight of the composition context to which the weigh percent refers, for example a wt % of a precursor is with respect to the context of an oxidative hair coloring composition or a tint composition of which the precursor is a part. Further, the sum of wt %'s of all the compounds (components), as described herein, in the respective compositions add up to 100 wt %.

The term "user" means the person preparing the hair coloring composition. The user may be, for example, a professional hair stylist working in a salon and is different from the subject on whose hair the composition is applied. The user, for example, may also be identical to the person on whose hair the composition is applied.

The term carbonate and/or bicarbonate means a compound of the formula $M_2CO_3$ and/or $MHCO_3$ wherein M is a cation of single positive charge or the symbol ($M_2$) of the formula $M_2CO_3$ is a single cation of double positive charge. M may be $NH_4$, an alkali metal cation such as sodium, potassium, lithium, an alkaline earth metal cation such as magnesium or barium, or an organic ammonium cation such as tetramethyl ammonium or guanidinium.

The anion terms peroxycarbonate and/or peroxybicarbonate are synonyms for percarbonate and/or perbicarbonate and have the anionic formulas $OC(O)OO^{-2}$, and $OC(O)OOH^{-1}$. These peroxy anions generate hydroxyl radicals (OH*), superoxide radicals ($O_2^{*-}$) and carbonate radicals ($CO_3^{*-}$). These radicals oxidize organic compounds by reacting with C—H or N—H or O—H moieties of organic compounds and to produce C*, N* or O* radical moieties which then produce oxidized forms.

The term "resorcinol" means 1,3-dihydroxybenzene as applied to cosmetic oxidative hair dye systems. The terms alkyl resorcinol and C1-C10 alkyl resorcinol mean 2 position C1-C10 alkyl resorcinol and/or a 4 position C1-C10 alkyl resorcinol as applied to cosmetic oxidative dye systems. The term halo or halogen resorcinol means resorcinol substituted at any position with a halogen atom including fluoro, chloro, bromo and/or iodo. The alkyl resorcinol and halo resorcinol are also termed herein alkyl and halo derivatives of resorcinol.

The term "oxidative hair dye composition" (as opposed to "oxidative hair coloring composition" according to the invention) means a composition of couplers and precursors for dyeing hair that includes resorcinol and/or (C1-C10) alkyl resorcinol and/or halogen resorcinol.

The term "color space" means the visible light spectrum measured by well-known parameters such L*a*b* values of the CIELAB color space spectrum. The Wikipedia explanation of the CIELAB color space is the understanding of this term applied here (Wikipedia, "CIELAB color space", Aug. 2, 2023). CIELAB color space, also referred to as L*a*b*, is a color space defined by the International Commission on Illumination (abbreviated CIE) in 1976. It expresses color as three values: L* for perceptual lightness and a* and b* for the four unique colors of human vision: red (magenta), green, blue and yellow. CIELAB is intended as a perceptually uniform space, where a given numerical change corresponds to a similar perceived change in color. While the LAB space is not truly perceptually uniform, it nevertheless is useful in industry for detecting small differences in color according to the Wikipedia description.

The CIELAB color space is a device-independent, "standard observer" model. The colors it defines are not relative to any particular device such as a computer monitor or a printer but instead relate to the CIE standard observer which is an averaging of the results of color matching experiments under laboratory conditions.

The CIELAB space is three-dimensional and covers the entire gamut (range) of human color perception. It is based on the opponent color model of human vision, where red (magenta) and green form an opponent pair and blue and yellow form an opponent pair. The lightness or luminescence value, L*, also referred to as "L star," defines dark at 0 and light at 100 and typically is expressed as L+ or positive indicating a progression to light or white with an increasing value as color develops and L- or negative indicating a progression to black or dark with a decreasing value as color develops. The a* axis is relative to the green-magenta opponent colors, with negative values toward green and positive values toward magenta. The b* axis represents the blue-yellow opponents, with negative numbers toward blue and positive toward yellow.

DETAILED DESCRIPTION OF THE INVENTION

The present invention is directed to embodiments of the oxidative hair coloring composition; embodiments of one or both of the combinable and/or combined components or parts which can form the oxidative hair coloring composition: a) a tint composition and b) an oxidizer composition; embodiments of the corresponding two parts characterized herein as a kit, and embodiments of the method of applying the oxidative hair coloring composition to hair such as anagenic hair.

Embodiments of the oxidative hair coloring composition for use in practice of embodiments of the method are free of resorcinol, alkyl resorcinol and halogen resorcinol and comprise a combination of at least the Aminol coupler and at least the MBB precursor and the L* mixture that delivers an L*a*b* scope of the CIELAB color space typically delivered by resorcinol based dye compositions. Embodiments of the method using the oxidative hair coloring composition display the pseudo-resorcinol property control in contrast to the continued L* darkening color development of dye compositions without resorcinol and without the amino acid ingredient of the L* mixture.

Embodiments of the oxidative hair coloring composition and its tint composition component for use in practice of the method comprise at least in part the precursor ingredient A, MBB and coupler ingredient B, Aminol as well as ingredient C, the L* mixture. The incorporation of additional secondary and/or subsidiary precursor and coupler ingredients with ingredients A and B and C while excluding resorcinol and its alkyl and/or halogen derivatives provides a series of color spectra typically delivered by resorcinol oxidative dye compositions. The examples described below show that the oxidative hair coloring composition produces an L*a*b* color spectrum scope like that of a resorcinol oxidative dye composition.

These ingredients A, B and C comprise:

A) precursor A comprising 2-methoxymethyl-p-phenylene diamine (MBB) of Formula I, its addition salts, its solvates and/or solvates of its salts;

Formula I

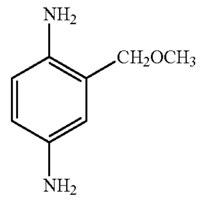

B) coupler B comprising hydroxyethyl-3,4-methylenedioxyaniline (Aminol) of Formula II, its addition salts, it solvates and/or solvates of its salts, Formula II

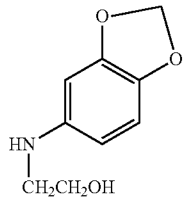

C) L* mixture C of a source of carbonate and/or bicarbonate, one or more amino acids and a source of an ammonium cation.

As previously stated, the oxidative hair coloring composition and corresponding method according to the invention do not contain, and are free of, resorcinol, alkyl resorcinol and halo resorcinol yet the oxidative hair coloring composition and its method have a pseudo-resorcinol property that controls the L* negative color progression.

The embodiments of method utilize embodiments of the oxidative hair coloring composition formed from the corresponding tint composition that comprise at least precursor A, coupler B and L* mixture C. Embodiments of oxidation feature of the method utilizing the oxidative hair coloring composition comprise the L* mixture C combined with hydrogen peroxide of the oxidizer composition component. The carbonate and/or bicarbonate source of the L* mixture C comprises an alkali metal salt, an alkaline earth metal salt and/or an inorganic or organic ammonium salt of carbonate and/or bicarbonate. Preferred alkali metals include sodium, potassium and lithium. Preferred alkaline earth metals include magnesium and barium. Calcium is not preferred because of the water insolubility of calcium carbonate/bicarbonate. The source of ammonium cation comprises a protonated C1-C3 di or tri alkyl ammonium halide or a C1-C3 tetraalkyl ammonium halide or $NH_4X$ where X is a halide anion or the ammonium cation may be the ammonium carbonate/bicarbonate. Most preferred is the combination of the sources for carbonate and/or bicarbonate and ammonium cation, namely ammonium carbonate and/or bicarbonate.

The one or more amino acids of the L* mixture C comprise any natural amino acid or homolog thereof. Amino acids include glycine, alanine, arginine, proline, serine, threonine, lysine, and preferred amino acids include glycine, alanine, arginine, proline and serine. Mixtures of the amino acids may also be employed. The sources of ammonium cation and carbonate/bicarbonate and the amino acid constitute ingredients of embodiments of the tint composition.

Embodiments of the oxidative hair coloring composition may or may not include the oxidizer composition component which includes hydrogen peroxide. Without inclusion of the oxidizer composition component, embodiments of the oxidative hair coloring composition constitute embodiments of the tint composition component. When formulated for oxidative coloring for hair, embodiments of the oxidative hair coloring composition constitute embodiments of the tint composition component set up to pursue oxidation activity. Typically, the set up may include the oxidizer composition component.

The Pseudo-Resorcinol Control

As discussed in the Background, resorcinol-based percarbonate oxidative hair dyes control the progress of color development and after a time period of up to about 30 minutes significantly reduce progress to a substantially steady state along the L* axis of the CIELAB color space spectrum. Attempts to follow this color development with oxidative hair dyes without resorcinol have failed. Managing the concentrations and mixtures of the precursor and alternative couplers without resorcinol produces hair dyes that continue to progress along the L* axis of the CIELAB color spectrum past 30 minutes or more. Consequently, careful professional management of the hair dye process is needed to avoid unevenly colored hair with non-resorcinol-based oxidative dyes.

Surprisingly, it has been found that the oxidative hair coloring composition and its corresponding method according to the invention, which comprise at least MBB, Aminol and the L* mixture but without resorcinol and its alkyl and halogen derivatives as described above, have a pseudo-resorcinol property for control of the L* progression of the downstream precursor-coupler couplings. This unique combination of the L* mixture joined with the precursor-coupler pair of MBB and Aminol without resorcinol and its alkyl and halogen derivatives interacts by management of the L* color progression to a substantially steady state. As a result, multi-coupler-precursor reactions of MBB-Aminol forming progressive L* negative products are not significant.

According to the invention, therefore, use of embodiments of the method to color hair with embodiments of the oxidative hair coloring composition produced by the combination of the tint composition component of at least MBB, Aminol and the L* mixture and the oxidizer composition component displays the pseudo-resorcinol control of L*a*b* coloration that mimics resorcinol control of L*a*b* color development of the CIELAB color space. This pseudo-resorcinol control enables facile application of these embodiments to the hair of a consumer without a concern for continued darkening color (L*) development afterward.

The examples below compare embodiments of the oxidative hair coloring compositions with the following variations:

A) without glycine and without resorcinol (described herein also as TC-1);

B) without glycine but with resorcinol (described herein also as TC-2);

C) with glycine and with resorcinol (described herein also as TC-3);

D) with glycine but without resorcinol (described herein also as TC-4).

The CIELAB color space results of these A-D variations show that:

1) The resorcinol free formula A without glycine (TC-1) continues to develop its CIELAB color space and progresses along the L* axis past 30 minutes.

2) The resorcinol formula B without glycine (TC-2) progresses along the L*axis for 20 to 30 minutes and then remains substantially steady.

3) Formula C with resorcinol and glycine (TC-3) adversely affects the CIELAB color space progress and color shade development relative to the desired progress and shade development shown by the color development of resorcinol formula B.

4) The resorcinol free formula D with glycine (TC-4) mimics the resorcinol formula B color development shade and progress because the resorcinol free formula D has a pseudo-resorcinol property.

These results show that resorcinol alone develops deep rich color and is an effective L* progression controller. Adding an amino acid such as glycine to this resorcinol formulation interacts with this control so that resorcinol control activity is in part blocked and deep, rich steady state color development produced by resorcinol alone is prevented. Non-resorcinol formulations without amino acid additives darken continuously, slowly and do not develop deep rich color. Amino acid such as glycine added to a non-resorcinol formulation delivers a pseudo-resorcinol control of a deep rich color and L* progression control like that produced by resorcinol.

Of course, if lighter and darker swatches are desired, higher and lower concentrations of the precursor and coupler ingredients may be mixed to provide batches of oxidative hair coloring composition that will provide darker and lighter L* values of the same color spectrum. The benefit is that the lighter and darker color development of these batches will also be controlled by the pseudo-resorcinol property so that the low concentration batches will have essentially the same L* value and the high concentration batches will have essentially the same L* value.

Secondary Precursor and Coupler

Further embodiments of the oxidative hair coloring composition and the tint composition and their inclusion for use in the practice of embodiments of the method of the invention comprise inclusion of the following secondary precursor PAP and one or more of the following secondary couplers DPE, MAP, AHT and EOAP. These additional secondary precursor and couplers are:

1. p-aminophenol (PAP), its addition salts, its solvates and/or solvates of its salts;
2. 2,4-diaminophenoxyethanol (DPE), its addition salts, its solvates and/or solvates of its salts;
3. m-aminophenol (MAP), its addition salts, its solvates and/or solvates of its salts;
4. 4-amino-2-hydroxy toluene (AHT), its addition salts, its solvates and/or solvates of its salts; and,
5. ethyl ortho-amino phenol (EOAP), its addition salts, its solvates and/or solvates of its salts.

Subsidiary Couplers and Precursors

In addition to inclusion of one or more of the secondary precursor and the couplers PAP, DPE, MAP, AHT and EOAP, or instead of inclusion of one or more of these secondary precursor and couplers, embodiments of the oxidative hair coloring composition and the tint composition and corresponding method may include one or more of the following additional subsidiary couplers and/or precursors.

Additional Subsidiary Couplers

The additional subsidiary couplers that can be included as described above in the oxidative hair coloring composition and the tint composition and corresponding method depend upon the color spectrum to be achieved. The one or more additional subsidiary couplers may increase the total concentration of all primary and secondary couplers present or may be a substitute for a portion of the other secondary couplers already present. The color shifts or changes resulting from such additional subsidiary couplers in combination with the ingredients A and B or with ingredients A and B and the secondary precursors and couplers present in the oxidative hair coloring composition are known and are managed by known parameters according to the desired color outcome and color space desired. Color change for the oxidative hair coloring composition may be accomplished by addition of one additional subsidiary coupler and/or by a mixture of two or more different further subsidiary couplers.

In certain embodiments of the present invention where a color shift of embodiments of the method is desired, the oxidative hair coloring composition and its tint composition component may comprise at least one or more additional subsidiary couplers selected from the group consisting of, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 2-amino-5-ethyl phenol, 6-hydroxybenzomorpholine, 6-amino-m-cresol, 6-amino-o-cresol, 2-amino-4-hydroxyethylaminoanisole, 1,3-bis-(2,4-diaminophenoxy) propane, 2,6-dihydroxyethyl-aminotoluene, 2,4-diamino-1,5-di(2-hydroxyethoxy)benzene, 1-naphthol, 2-methyl-1-naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindoline, phenyl methyl pyrazolone, hydroquinone, 4-formyl-1-methylquinolinium-p-toluenesulfonate and addition salts, solvates and/or solvates of salts thereof.

Additional Oxidative Precursors

In embodiments of the oxidative hair coloring composition and its tint composition component where a color shift of embodiments of the method is desired, the oxidative hair coloring composition and the corresponding tint composition may additionally comprise at least one additional subsidiary precursor. The one or more additional subsidiary precursors may increase the total concentration of all primary and secondary precursors present or may be a substitute for a portion of the other secondary precursors already present. The color shifts or changes resulting from such additional subsidiary precursors in combination with the ingredients A and B or with ingredients A and B and the secondary precursors and couplers present in the oxidative hair coloring composition are known and managed by known parameters according to the desired color outcome and color space desired. This color shift for the oxidative hair coloring composition may be accomplished by addition of one additional subsidiary precursor and/or by a mixture of two or more different further subsidiary precursors.

In the embodiments of the presently claimed invention where a color shift of embodiments of the method is desired, the embodiments of the oxidative hair coloring composition and its tint composition component may additionally comprise at least one or more additional subsidiary precursors selected from the group consisting of hydroxyethyl-p-phenylenediamine sulphate, hydroxypropyl bis(n-hydroxyethyl-p-phenylenediamine), 2-chloro-p-phenylenediamine, p-methylaminophenol, 4-amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol 2,3-diamino dihydroxypyrazolo pyrazolone dimethosulfonate, 4,5-diamino-1-hexylpyrazol, hydroxypropyl-p-phenylenediamine, dimethylpiperazinium aminopyrazolopyridine chloride hydrochloride, methylimidazoliumpropyl p-phenylenediamine, hydroxyethoxy aminopyrazolopyridine and addition salts, solvates and/or solvates of salts thereof.

In embodiments of the oxidative hair coloring composition and its tint composition component where a color shift of embodiments of the method is desired, the oxidative hair coloring composition and the corresponding tint composition may additionally comprise combinations of the above described one or more additional subsidiary precursors and one or more additional subsidiary couplers. The color shifts or changes resulting from combinations of such additional subsidiary couplers and additional subsidiary precursors in combination with the ingredients A and B or with ingredients A and B and the secondary precursors and couplers present in the oxidative hair coloring composition are known and managed by known parameters according to the desired color outcome and color space desired.

Concentrations

Embodiments of the invention may comprise concentrations of the precursor MBB ranging from about 0.1 wt % to about 10 wt %, preferably from about 0.5 wt % to about 6 wt %, more preferably from about 1.0 wt % to about 4 wt %, most preferably from about 1.5 wt % to about 3 wt %, especially most preferably about 0.1 wt % to about 3 wt % relative to the total weight of the oxidative hair coloring composition.

Embodiments of the invention may comprise concentrations of the coupler AMINOL ranging from about 0.1 wt % to about 5 wt %, preferably from about 0.5 wt % to about 4 wt %, more preferably from about 0.5 wt % to about 3 wt %, most preferably from about 0.5 wt % to about 2 wt %, especially most preferably about 0.1 wt % to about 2 wt % relative to the total weight of the oxidative hair coloring composition.

When one or more of the secondary precursor and/or couplers, PAP DPE, MAP AHT AND EOAP, is/are included in embodiments of the oxidative hair coloring composition, their concentrations may range as follows:

a) PAP at a concentration of about 0.1 wt % to about 3 wt %, preferably about 0.2 wt % to about 1.5 wt %, preferably about 0.2 wt % to about 1 wt %, more preferably about 0.01 wt % to about 0.5 wt %;

b) DPE at a concentration of about 0.1 wt % to about 3 wt %, preferably about 0.1 wt % to about 2.5 wt %, more preferably about 0.1 wt % to about 2.0 wt %, most preferably about 0.1 wt % to about 1.5 wt %;

c) MAP at a concentration of about 0.1 wt % to about 3.0 wt %, preferably about 0.1 wt % to about 2 wt %, more preferably 0.1 wt % to about 1.5 wt %, most preferably about 0.1 wt % to about 1 wt %;

d) AHT at a concentration of about 0.05 wt % to about 1.5 wt %, preferably about 0.05 wt % to about 1 wt %, more preferably about 0.05 wt % to about 0.5 wt %; most preferably about 0.05 wt % to about 0.2 wt %; and e) EOAP at a concentration of 0.01 wt % to 2 wt %, preferably about 0.01 wt % to about 1.5 wt %, more preferably about 0.01 wt % to about 0.5 wt %, most preferably about 0.01 wt % to about 0.3 wt %.

Especially most preferably, the embodiments of the concentrations of the secondary precursors and couplers of embodiments of the oxidative hair coloring composition comprise:

a) PAP at a concentration of about 0.2 wt % to about 0.5 wt %;

b) DPE at a concentration of about 0.1 wt % to about 1.5 wt %;

c) MAP at a concentration of about 0.1 wt % to about 0.5 wt %;

d) AHT at a concentration of about 0.05 wt % to about 0.15 wt %; and e) EOAP at a concentration of about 0.1 wt % to about 0.5 wt %.

The concentrations of subsidiary precursors and couplers follow the foregoing concentrations of PAP DPE, MAP AHT AND EOAP according to their function as precursors or couplers. Choice among these subsidiary precursors and couplers depends upon the color space to be covered. The colors they provide in combination with MBB and Aminol are reported in the public literature and patents.

The exemplary comparisons described below show that practice of embodiments of the method using the oxidative hair coloring composition produces essentially the same a*b* color space as well as the L* progression control that is produced by a method using a comparative oxidative hair dye composition with resorcinol and optional alkyl and halo resorcinol derivatives. This is a surprising achievement given the expectation that no oxidative hair dye composition without resorcinol can develop the breadth of tint and shade and L* progression control produced by resorcinol.

Medium

The medium of the embodiments of the oxidative hair coloring composition, the corresponding method and the kit of the tint composition component and the oxidizer component may be a "cosmetically acceptable aqueous or aqueous-organic medium." Exemplary media include deionized water alone and deionized water in combination with a liquid organic solvent such as one or more of a C1-C4 mono-alcohol, a C2-C6 diol, a C3-C6 triol, a C3-C4 ketone and similar organic solvents typically used as cosmetically acceptable media provided that such organic solvents are not chemically reactive with any of the components of the oxidative hair coloring composition. Typical organic solvents for mixture with water to form a cosmetically acceptable aqueous-organic medium include ethanol, isopropanol, n-propanol, butanol, glycerin, ethylene or propylene glycol, and hexane glycol.

The medium concentration for the oxidative hair coloring composition may be in a range of ≥30.0 to ≤95.0 wt. %, preferably in an amount in the range of ≥35.0 to ≤92.0 wt. %, more preferably in an amount in the range of ≥40.0 to ≤90.0 wt. %, based on the total weight of the oxidative hair coloring composition. The concentration of organic solvent in water for the aqueous-organic medium may be in a range of from about 1% to about 50%, preferably about 1% to about 25% by volume relative to the total volume of the medium.

Oxidizing Agent

The formation of the color in the anagenic hair is accomplished by oxidation of the precursor or precursors and their reaction with the coupler or couplers to form large dye polymer molecules inside the hair strands. The starting material for the oxidizing agent for the oxidative hair coloring composition is hydrogen peroxide. The hydrogen peroxide at basic pH combines with the carbonate/bicarbonate source of the tint composition component to form in situ peroxymonocarbonate/peroxybicarbonate. The peroxymonocarbonate/peroxybicarbonate is the active oxidizing agent of the oxidative hair coloring composition according to the invention.

Because this oxidative reaction takes place upon the combination of the oxidizing agent and the precursors and oxidative couplers, the hydrogen peroxide is typically maintained in a separate composition until the oxidative hair coloring composition is to be applied to anagenic hair. The separation of the oxidizing and tinting components of the oxidative hair coloring composition is characterized herein by the description of the kit. The kit embodiments comprise (I) the tint composition of at least ingredients A, B, and C (carbonate and/or bicarbonate source, amino acid, ammonium source, and alkalizing agent) and additional optional chassis components and (II) the separate oxidizer composition component of at least hydrogen peroxide.

Typically, the hydrogen peroxide as the oxidizer composition of the kit is combined with the tint composition of the kit immediately before its application to anagenic hair. Under ordinary conditions, embodiments of the oxidizer composition as a separate composition include ancillary carrier ingredients such as an aqueous or organo-aqueous medium along with a fatty alcohol, an anionic surfactant, a hydrocarbon, a buffer and acid. Exemplary ingredients for embodiments of this oxidizer component comprise water, cetearyl alcohol, sodium cetearyl sulfate, paraffinum, salicylic acid, buffer of disodium phosphate/phosphoric acid, citric acid and etidronic acid. The pH of the oxidizer composition is rendered acidic by inclusion of cosmetically acceptable organic and/or inorganic acids and acidic buffer. When the oxidizer composition component is combined with the tint composition component, the alkalizing agent of the tint composition changes the pH of the resulting mixture to basic. Additionally, the hydrogen peroxide converts the carbonate/bicarbonate source to percarbonate/perbicarbonate anions.

In one embodiment, the hydrogen peroxide in the oxidative hair coloring composition is preferably present in an amount in the range of about 1.0 wt. % to about 12.0 wt. %, more preferably in an amount in the range from of about 1.0 wt. % to about 8.0 wt. % based on the total weight of the oxidative hair coloring composition. Because the oxidizing agent or oxidizer is maintained in as a separate composition until the oxidative hair coloring composition is to be applied to hair, as explained above, the concentration of hydrogen peroxide in the separate oxidizer composition of the kit is determined by back calculation from its final concentration to be used in the oxidative hair coloring composition. For example, if the final concentration of hydrogen peroxide is to be 6 wt % in the oxidative hair coloring composition, the oxidizer and tint components are combined at a weight ratio of 1:1, and the hydrogen peroxide is a 50 wt % aqueous solution, the amount of 50 wt % aqueous solution of hydrogen peroxide to be added to the oxidizer component will provide a 12 wt % solution of hydrogen peroxide in the oxidizer component. If the weight of the oxidizer composition with hydrogen peroxide is to be 100 gm, 12 gm of hydrogen peroxide as 24 gm of 50 wt % aqueous hydrogen peroxide is added to this oxidizer composition without hydrogen peroxide (e.g., 76 gm oxidizer composition without the 50% hydrogen peroxide solution) to enable a 6 wt % hydrogen peroxide final concentration in the oxidative hair coloring composition.

Chassis

The embodiments of the oxidative hair coloring composition and corresponding method also may optionally include one or more ancillary cosmetic carrier ingredients also known as chassis ingredients. In addition to the alkalizer (component I as at least a part of the L* mixture), the chassis ingredients include but are not limited to one or more anionic and/or nonionic surfactants (component J), one or more fatty substances (component K), one or more chelators (component L), one or more viscosity control agents (component M), one or more conditioners (component N), one or more humectants/emulsifiers, one or more antioxidants and one or more pH control agents as well as other usual and typical ancillary ingredients well-known for use with for oxidative hair dye technology.

Alkalizer, Component I, for the L* Mixture

The alkalizer or alkalizing agent of embodiments of the oxidative hair coloring composition and corresponding method is present in embodiments of the tint composition carrying the dye components and ancillary carriers and not in the oxidizer composition (e.g., present in the tint composition of the kit described above).

Embodiments of the oxidative hair coloring composition and embodiments of the tint composition as well as the corresponding method include component I, an additional alkalizer or alkalizing agent, such as sodium hydroxide, as an additive to the L* mixture C of the oxidative hair coloring composition. The L*mixture comprises a source of carbonate and/or bicarbonate, one or more amino acids and a source of an ammonium cation.

The additional alkalizer, sodium hydroxide, may be present in the oxidative hair coloring composition in an amount in the range of about 0.1 wt. % to about 10.0 wt. %, preferably in an amount in the range of about 0.1 wt. % to about 7 wt. %, particularly preferred in an amount in the range of about 1.0 wt. % to about 6 wt. %, and most preferred in an amount in the range of about 1.0 wt. % to about 3 wt. %, in each case based on the total weight of the oxidative hair coloring composition. The amount of sodium hydroxide in the tint composition is determined by the dilution factor and the neutralization factor resulting from the mixing of the tint composition and the oxidizer composition to form the oxidative hair coloring composition.

The carbonate/bicarbonate may be present in the oxidative hair coloring composition in an amount that will essentially, to completely, form percarbonate/perbicarbonate when combined with the weight percentage of hydrogen peroxide present in the oxidizer composition component. Typically, the hydrogen peroxide and carbonate/bicarbonate in embodiments of the oxidative hair coloring composition are present at a molar ratio of 1:1 to 1:1.2 with the carbonate/bicarbonate being present preferably at a slight molar excess. The concentration of carbonate/bicarbonate in embodiments of the tint composition may be back calculated from this molar ratio for the oxidative hair coloring composition.

Inclusion of the one or more amino acids with the alkalizer and carbonate and/or bicarbonate source and ammonium source provides the L* mixture with additional alkalizer. When the L* mixture is combined with MBB and Aminol to form the tint composition and then added to the oxidizer composition, the resulting oxidative hair coloring composition has the property of pseudo-resorcinol control. Because the tint composition is basic, the amino acids are present as alkali or alkaline earth metal salts.

The amino acids of the L* mixture are present at a total concentration of from about 0.01 wt % to about 15.0 wt %, preferably 0.1 wt % to about 10.0 wt %, more preferably from about 1 wt % to about 6 wt % or 1.5 wt % to 4 wt % with minimum concentrations beginning at 0.1 wt %, 0.5 wt %, 1 wt %, 2 wt %, or 3 wt % relative to the total weight of the oxidative hair coloring composition.

When the oxidative hair coloring composition is formulated as a kit comprising the tint composition and the oxidizer composition as described above, the alkalizer, the source of carbonate/bicarbonate and the one or more amino acids are present in the tint composition. When the tint composition is combined with the oxidizer composition, the concentrations of the components of the tint composition are diluted according to the volume or weight ratio of the tint composition to the oxidizer composition. Accordingly, the concentrations of the alkalizer, the source of carbonate/bicarbonate and the one or more amino acid(s) needed in the tint composition may be calculated as described above from the desired final concentrations and basic pH of the oxidative hair coloring composition and the dilution ratio of the tint and oxidizer compositions.

Component J—Anionic, and Nonionic Surfactant and Optional Cationic Surfactant

The anionic, and nonionic surfactant provides a solubilizing function for components of the oxidative hair coloring composition as well as the ingredients of the kit constituents, e.g., the tint and oxidizer compositions, that are insoluble, slightly soluble and moderately soluble in water. The anionic and/or nonionic surfactants also are believed to participate in the transport of the components of the oxidative hair coloring composition onto and into the strand of anagenic hair at least in part by mingling and/or interacting with the sebum, f-layer and strand surface compounds present on anagenic hair.

The anionic surfactant spans the categories of phosphate anionic surfactant, sulfate anionic surfactant and carboxyl anionic surfactant such as but not limited to one or more alkyl and/or polyoxyalkyl alkyl phosphates and/or one or more alkyl sulfates and/or polyoxyalkylene alkyl sulfates and/or one or more alkyl carboxylates and/or polyoxyalkylene alkyl carboxylates.

The nonionic surfactant spans the categories of polyethoxyalkylether nonionic surfactant, alkamido betaine zwitterionic surfactant, polysorbate surfactant, glucoside and polyglucoside nonionic surfactant, fatty alkyl pyrrolidone nonionic surfactant, polyoxyalkylene fatty acid ester nonionic surfactant, alkylpolyoxyalkylenalkanamidoalkyl alcohol nonionic surfactant.

When included, the cationic surfactant spans the categories of higher alkyl di and/or trimethyl ammonium cationic surfactant, poly(dimethyliminoalkylenyl) alkane cationic surfactant.

Representative examples of anionic surfactants include salts (such as alkaline salts, for example, sodium salts, ammonium salts, amine salts, amino alcohol salts and magnesium salts) of the following compounds: alkyl phosphates, alkyl ether phosphates, C8 to C30 alkyl phosphate, C8 to C30 alkyl polyoxyalkyl-alkyl ether phosphate or mixtures thereof, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates; alkyl succinates, alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyl methylaminopropionate; acyl isethionates, N-acyl taurates; acyl lactylates; carboxyalkyl ether of alkyl polyglucosides; alkyl lecithin derivatives. The alkyl or acyl radical of all of these various compounds, for example, comprises from about 8 to 30 carbon atoms, and the aryl radical, for example, is chosen from phenyl and benzyl groups.

Preferred exemplary anionic surfactants include alkyl phosphates, polyoxyalkyl-alkyl ether phosphates, alkyl ether sulphates, alkyl glyceryl sulphonates, N-acyl sarcosinates, N-acyl taurates, acyl lactylates and carboxyalkyl ether of alkyl polyglucosides. Yet, more preferable surfactants are selected from alkyl phosphates and polyoxyalkyl-alkyl ether phosphates having an average 1 to 20, 1 to 10 or 1 to 3 ethylene oxide units.

More preferred phosphate anionic surfactants include dicetyl phosphate, ceteth-10 phosphate alone or together or in combination with cetearyl alcohol having the trade name Crodafos sold by Croda International, Snaith, United Kingdom.

Most preferred sulfate anionic surfactants include laureth-2 to 200 sulfate, cocyl isethionate and lauryl sulfate.

Representative examples of the nonionic surfactants include polyoxyalkylene-fatty alcohol esters of fatty acids, alkyl polyoxyalkylene ethers which are derived from C1-C6-alcohols or from C7-C30-fatty alcohols, alkylaryl alcohol polyoxyethylene ethers, alkoxylated animal and/or plant fats and/or oils, glycerol esters, alkylphenol alkoxylates, fatty amine alkoxylates, fatty acid amide and fatty acid diethanolamide alkoxylates, ethoxylates thereof, sugar surfactants, sorbitol esters, polyoxyethylene sorbitan fatty acid esters, alkyl polyglycosides, N-alkylgluconamides and alkyl methyl sulfoxides.

Preferred exemplary nonionic surfactants include steareth-2 to 200, octadeceth-2 to 200, laureth-2 to 200, undeceth-2 to 200, pareth-2-200, cocamidopropyl betaine, polysorbate −2 to 80 polyoxyethylene, lauryl pyrrolidone and any combination thereof. More preferred exemplary nonionic surfactants include steareth 2 to 200, octadeceth 2-200 (also known as Brij 2-200) and pareth 2-200 and any combination thereof.

The optional cationic surfactant useful as a surfactant and/or conditioning agent with the oxidative hair coloring composition may be one or more quaternary ammonium salts or amido-amines having at least one fatty chain containing at least about 20 carbon atoms and mixture thereof. Preferably, the surfactant component J does not include a cationic surfactant as either a surfactant or as a conditioning agent. Moreover, preferably, the oxidative hair coloring composition is free of a cationic surfactant.

When optionally included, and preferably separately as a conditioning agent, the cationic surfactant may be any one or more of the quaternary ammonium salts useful as cationic surfactants for the composition which follow the general formula $N^+(R^1R^2R^3R^4)X^-$: wherein, $R^1$ is selected from linear and branched radicals comprising about 20 to 30 carbon atoms, $R^2$ is selected from linear and branched radicals comprising about 20 to 30 carbon atoms or the same group as radicals $R^3$ to $R^4$, the radicals $R^3$ to $R^4$, which can be identical or different, are selected from linear and branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein $X^-$ is an anion selected from halides, such as chloride, bromide and iodide) ($C_2$-$C_6$)alkyl sulphates, such as methyl sulphate, phosphates, alkyl and alkylaryl sulphonates, and anions derived from organic acids, such as acetate and lactate.

Representative examples of a cationic surfactant for use with the oxidative hair coloring composition include behentrimonium chloride, behenamidopropyltrimonium methosulfate, stearamidopropyltrimonium chloride, arachidtrimonium chloride and mixtures thereof.

Generally, the amido-amine cationic surfactants follow the general formula $R'^1—CONH(CH_2)_nNR'^2R'^3$: wherein, $R'^1$ is selected from linear and branched radicals comprising about 20 to 30 carbon atoms, the radicals $R'^2$ and $R'^3$, which can be identical or different, are selected from hydrogen, linear and branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein n is integer from 1 to 4.

Representative examples of the amido-amine cationic surfactant include behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Preferably, the surfactant, component J, is an anionic surfactant or non-ionic or a combination of both. More preferably, the surfactant component J is a combination of dicetyl phosphate, ceteth-10 phosphate together with cetearyl alcohol optionally with a non-ionic surfactant such as cetereth-2-200, brij-2-200 and/or pareth-2-200.

Component K, Fatty Substance

The fatty substance, component K, includes lipophilic/hydrophobic substances that are insoluble or slightly soluble in water. The fatty substances are soluble in organic solvents such as chloroform, ethanol, or benzene. The fatty substances may be liquids or solids, usually low melting solids at STP. The fatty substances include the categories of C8-C36 alkyl and alkenyl alcohols. One, several and/or all of these categories of fatty substance may be included in the composition. The fatty substances provide hair conditioning effects and ameliorate the action of the oxidizer on the anagenic hair causing the anagenic hair to be brittle, unruly and subject to breakage. Additionally the one or more substances can act as carriers of dye actives to deliver the dye actives to the anagenic hair surfaces. One or more of the categories of fatty substances may be combined with oxidative hair coloring composition. Typically at least some of the categories of the fatty substances may be present in the oxidizer composition of the kit as long as they are not reactive with the oxidizer and all may be present in the tint composition.

In one embodiment of the invention, the fatty alcohol preferably may be a saturated or unsaturated linear or branched C8 to C36 fatty alcohol, preferably saturated and preferably linear, and preferably a C12 to C 20 linear saturated mono alcohol, and more preferably selected from the group consisting of cetyl alcohol, stearyl alcohol, cetearyl alcohol (mixture of cetyl and stearyl alcohols) or behenyl alcohols or mixtures thereof.

According to the present invention, the oxidative hair coloring composition may include none of the fatty substances or may include one or more wherein the concentration of each may range from about 0.1 wt % to about 20 wt %, preferably from about 0.2 wt % to about 15 wt %, more preferably from about 0.5 wt % to about 12 wt % relative to the total weight of the composition. The total concentration of all fatty substances in the composition may range from about 1 wt % to about 50 wt %, preferably from about 1 wt % to about 25 wt % relative to the total weight of the composition.

Component (L)

The chelant or chelator, component L, includes any cosmetically acceptable organic or inorganic compound that is capable of complexing metal ions. Included are a single chelator as well as mixtures of chelators. The one or more chelators typically are included in the oxidative hair coloring composition and in both of the tint and oxidizer compositions of the kit.

Chelants or chelators useful for inclusion in both of the tint and oxidizer compositions as well as in the oxidative hair coloring composition and corresponding methods include at least one of ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), methylglycine diacetic acid (MGDA), 1-hydroxyethylidene-1,1-diphosphonic acid (HEDP), dimethyl glucamine (DMG), diethylenetriamine penta(methylene phosphonic acid (DTPMP), glutamate diacetate (GLDA) and etidronic acid (HEDP) as well as the salt or salts thereof, a derivative or derivatives thereof, and/or any combination thereof. Preferred chelators for inclusion in the tint, oxidizer and oxidative hair coloring compositions include EDDS, MGDA, GLDA and HEDP. In one embodiment of the presently claimed invention, the chelant is EDDS or MGDA, more preferably is (S,S)-EDDS or MGDA and their salts thereof.

The concentration of the chelator or chelant in embodiments of the oxidative hair coloring composition and corresponding method may range about 0.20 wt. % to about 1.5 wt. % to about 3 wt. %, based on the total weight of the oxidative hair coloring composition. The concentrations of chelator in the tint and oxidizer compositions of the kit for preparing the oxidative hair coloring composition may be back calculated from the concentration for the oxidative hair coloring composition.

Component M

Embodiments of the oxidative hair coloring compositions and methods of the present invention preferably include a thickener, component M, in particular a polymeric thickener in an amount that is sufficient to impart a viscosity to the composition that allows for its ready application to hair without unduly dripping off the hair, as is known in the art. Typically, such an amount will be at least about 0.1 wt. %, in some embodiments, at least about 0.5 wt. %, in other embodiments, at least about 1.0 wt. %, based on the total weight of the oxidative hair coloring composition.

Exemplary thickeners for use with the present invention are organic thickeners, including but not limited to: xanthan, guar, hydroxypropyl guar, scleroglucan, methyl cellulose, ethyl cellulose (available as AQUACOTE®, hydroxyethyl cellulose (NATROSOL®), carboxymethyl cellulose, hydroxypropylmethyl cellulose, microcrystalline cellulose, hydroxybutylmethyl cellulose, hydroxypropyl cellulose (available as KLUCEL®), hydroxyethyl ethyl cellulose, cetyl hydroxyethyl cellulose (available as NATROSOL® Plus 330), N-vinylpyrrolidone (available as POVIDONE®), Acrylates/Ceteth-20 Itaconate Copolymer (available as STRUCTURE® 3001), hydroxypropyl starch phosphate (available as STRUCTURE® ZEA), polyethoxylated urethanes or polycarbamyl polyglycol ester (e.g. PEG-150/Decyl/SMDI copolymer (e.g. ACULYN® 44), PEG-150/Stearyl/SMDI copolymer (available as ACULYN® 46), trihydroxystearin (available as THIXCIN®), acrylates copolymer (e.g. available as ACULYN® 33) or hydrophobically modified acrylate copolymers (e.g. Acrylates/Steareth-20 Methacrylate Copolymer (available as ACULYN® 22), acrylates/steareth-20 methacrylate crosspolymer (available as ACULYN® 88), acrylates/vinyl neodecanoate crosspolymer (available as ACULYN® 38), acrylates/beheneth-25 methacrylate copolymer (available as ACULYN® 28), acrylates/C 10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain.

In another embodiment of the present invention, the preferred thickener is an organic thickener which may be cellulose-based thickeners (hydroxyethycellulose, hydroxypropyl cellulose, carboxymethylcellulose), guar gum and derivatives thereof (hydroxypropyl guar), gums of microbial origin (xanthan gum, scleroglucan gum), crosslinked homopolymers of acrylic acid or of acrylamido-propanesulfonic acid, and cellulose-based thickeners, such as hydroxyethylcellulose. The preferred organic thickener may be present in an amount ranging from about 0.1 to about 20 wt %, preferably from about 0.1 to about 5 wt % based on the total weight of the composition.

Component (N)

Optionally, embodiments of the oxidative hair coloring composition and corresponding method may include a conditioner for softening and at least in part protecting the hair from untoward effects of oxidation. The conditioner component N may be a cationic surfactant as described above for component J. While a cationic surfactant may function as component J for solubilizing components of the oxidative hair coloring composition, it is preferable not to include a cationic surfactant if the purpose is solubilizing components of the oxidative hair coloring composition. As described below, use of a cationic surfactant as a conditioner, e.g., component N, is appropriately practiced according to the invention by providing a separate conditioning unit of component N along with the kit of the two oxidative hair coloring composition components, the tint component unit and the oxidizer component unit.

When used as a conditioner and especially as a separate conditioner unit, embodiments of the conditioning component N may be selected from quaternary ammonium and tertiary amine compounds, amido ammonium and tertiary amine compounds, mono, di and polysaccharides with quaternary ammonium or tertiary amine groups, or any mixture thereof.

Non-limiting classes of these cationic surfactants include mono or di fatty alkyl or alkenyl quaternary ammonium and tertiary amine compounds, mono or di polyol quaternary ammonium and tertiary amine compounds, mono or di fatty alkyl or alkenyl benzyl quaternary ammonium and tertiary amine compounds, fatty alkyl or alkenyl aryl, polyol quaternary ammonium and tertiary amine compounds, polyol mono, di or tri saccharide alkyl quaternary ammonium and tertiary amine compounds, tertiary or quaternized aminoalkyl fatty alkyl or alkenyl ester or amide compounds, phenoxy-alkyl fatty alkyl or alkenyl quaternary ammonium and tertiary amine compounds, hydrolyzed starch with terminally quaternized ammonium and tertiary amine compounds, multi-polyol cellulose with terminal quaternized ammonium and tertiary amine compounds, sucrose, lactose mono and disaccharides, arabic, ghatti, guaicum, guar, karaya, locust bean and xanthan gums derivatized with terminal quaternized ammonium and tertiary amine compounds, and similar hydrophobic tail with cationic head organic compounds. The classes of cationic surfactants with tertiary amine groups may be protonated by the media or by organic acid to form cationic groups.

Examples of these cationic surfactants may be selected from and/or include cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, benzalkonium chloride, benzododecinium bromide, cetalkonium chloride, dicedyldimenthlammonium chloride dimethyldioctadecylamminum chloride, dioleoyl-3-trimethyl ammonium propane, lauryl methyl gluceth-10 hydroxylpropyl dimonium chloride N-oleyl-1,3-propane diamine, stearalkonium chloride and mixtures thereof. Additional cationic surfactants include cetyl trimethyl ammonium chloride available, for example, with trade name CA-2350 from Nikko Chemicals and CTAC 30KC available from KCl, stearyl trimethyl ammonium chloride with trade name Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methyl) pyridinium chloride; hydrophilically substituted cationic surfactants having the following INCI designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and any combination thereof.

Additional Ingredients

Embodiments of the oxidative hair coloring composition and corresponding method according to the invention may further include typical and usual ingredients such as humectants, emulsifiers, pH control agents, antioxidation agents and sunscreen/whitening agents. These ingredients are known in the art for use with oxidative dye developments.

The humectants/emulsifiers typically are water soluble hydroxylic organic compounds with low vapor pressure and tend adhere to keratin fibers through hydrogen bonding so that at least in part they may remain on the anagenic hair after rinsing away the oxidative hair dye composition. Exemplary humectant/emulsifiers include a polyhydric, trihydric and/or dihydric alcohol (i.e., a per-hydroxy alkane, a triol or a diol) or a dimer, trimer tetramer, pentamer thereof. The polyol may be liquid or solid. The polyhydric alcohol may be a C4-C8 alkane with each carbon substituted by a hydroxyl group or a dimer or trimer thereof. The trihydric alcohol may be a C3 to C8 alkane substituted by three hydroxyl groups or a dimer or trimer thereof. The dihydric alcohol may be a C2 to C8 alkane substituted by two hydroxyl groups or a dimer or trimer thereof. Preferably, the trihydric and dihydric alcohols in pure form and without dilution with water display liquid and/or flowable properties at ambient conditions.

Exemplary polyhydric alcohols include sugar alcohols such as but not limited to erythritol, xylitol and sorbitol. Exemplary triols may be selected from propylene triol (glycerin), 1,2,3-butylene triol, 1,2,5-pentylene triol and/or 1,3,6-hexylene triol and any combination thereof. Exemplary diols may be selected from ethylene glycol, 1,2-propylene diol, 1,3 propane diol, 1,2- and 1,3-butane diol, 1,2 pentane diol, diethylene glycol, dipropylene glycol and any combination thereof. Preferred polyols include sorbitol, glycerin (propyl triol), 1,2,3-butanetriol, ethylene glycol diethylene glycol, propylene glycol, lanolin alcohol, hexylene glycol, dipropylene glycol and any combination thereof. A more preferred polyol is lanolin alcohol, glycerin, 1,2 propylene diol, 1,3 propylene diol and any combination thereof.

The agents for pH control may be added to the tint and oxidizer compositions that may be combined to form the oxidative hair coloring composition. The pH control agents manage the pH of the tint and oxidizer compositions so as to provide a basic pH for the tint composition and an acidic pH for the oxidizer composition. When the tint and oxidizer compositions are combined to form the oxidative hair coloring composition, the pH may need rebalancing to a pH of from slightly above 7 to 10, preferably from about 7.5 to about 10, more preferably from about 9 to about 10, most preferably from about 9 to about 9.5. Establishment of a basic pH of the oxidative hair coloring composition facilitates the oxidative function of the oxidizer while establishment of an acidic pH of the oxidizer composition prevents facile decomposition of the hydrogen peroxide or other peroxide producing compound. Agents for pH control include sodium hydroxide, citric acid, etidronic acid and combinations thereof.

Additional, optional antioxidant inclusion with the tint composition used to form embodiments of the oxidative hair coloring composition and corresponding method according to the invention prevents undesirable air oxidation of the precursor and coupler compounds of the tint while the tint composition is in package form, is on the shelf and before its use with the oxidizer composition. Useful antioxidants for this purpose include ascorbic acid, ascorbic acid stereoisomers, sodium sulfite, vitamin E and combinations thereof.

Inclusion of sunscreen agents provides protection of the colored hair from bleaching by the sun. Agents such as mica, titanium oxide and similar light reflecting materials or light absorbing materials such as benzophenone-4 and/or ethylhexyl methoxycinnamate may be included for this purpose.

Additionally, embodiments of the present invention may include penetrants; fragrances; dispersants; film-forming agents; ceramides; preserving agents; and opacifiers in the composition.

EXEMPLARY EMBODIMENTS

In one embodiment of the presently claimed invention, the method utilizing the oxidative hair coloring composition is obtained by mixing the tint composition and oxidizer composition components. The exemplified tint composition comprises preferably at least one additional alkalizing agent and at least the mixture of primary precursor A, the primary coupler B, the L* mixture C and the secondary precursor and couplers described above. The oxidizer composition comprises at least the hydrogen peroxide (component H) with non-reactive components of the chassis as described above. The oxidative hair coloring composition is packaged as a two-component system of tint composition and oxidizer composition components so that combining these two components produces an embodiment of the ooxidative hair coloring composition according to the invention.

Embodiments of the tint and oxidizer compositions may be formulated with appropriate carrier ingredients herein termed chassis components to deliver a composite set of carrier ingredients for the oxidative hair coloring composition that will facilitate and promote oxidative reaction of the precursor and coupler components, opening of the anagenic hair cuticles and enabling transport of the reactive agents to the cores of the anagenic hair strands.

A first exemplary chassis construction for this purpose may be designed in a cosmetically acceptable aqueous or aqueous-organic medium with a phosphate anionic surfactant of dicetyl phosphate and ceteth-10 phosphate preferably combined as Crodafos, cetearyl alcohol, glycerin and propylene glycol, ascorbic acid, citric acid, erythorbic acid, etidronic acid, EDTA, EDDS-3 Na, MGDA, GLDA, sodium hydroxide and xanthan gum. These chassis components may be combined as appropriate and consistent with the coupler/precursor ingredients and L* mixture C of the tint composition and the hydrogen peroxide ingredient of the oxidizer composition considering the chemical oxidizing potential and the required acidic pH of the oxidizer composition before its combination with the tint composition.

A further exemplary chassis construction has been found to enable at least substantially uniform root to tip coverage of the composition according to the invention. This chassis construction includes a combination of dicetyl phosphate, ceteth-10 phosphate (Crodafos) as the phosphate surfactant, cetearyl alcohol, steareth-200 as the nonionic surfactant, and xanthan gum as the viscosity control, glycerin, propylene glycol, ascorbic acid, EDDS-3Na, EDTA and/or MGDA and/or GLDA and sodium hydroxide.

The highly preferred chassis for the tint composition part of the oxidative hair coloring composition includes about 0.2 wt % to about 25 wt %, preferably about 0.2 wt % to about 20 wt % of a mixture of dicetyl phosphate and ceteth-10 phosphate and cetearyl alcohol at a wt % ratio of about 1 to about 15 wt %, preferably about 1.5 to about 10 wt % of each of the two phosphates and a remainder of cetearyl alcohol relative to the total weight of the mixture; xanthan gum at about 0.1 wt % to about 0.2 wt %, steareth-200 at about 0.2 wt % to about 0.5 wt %, with the alkalizer sodium hydroxide, one or more of MGDA, GLDA, EDDS and DTPMP and propylene glycol/water.

These exemplary chassis constructions do not contain fatty acid ester or fatty acid or a cationic surfactant conditioner. An organic solvent with water completes these highly preferred chassis constructions.

It is believed that this highly preferred chassis construction is adapted with the Aminol coupler along with the other couplers to deliver responsive coloration methods to hair strands to roots and/or from roots to tips. In contrast, it is believed that chassis constructions based on nonionic surfactants alone, sulfate or carboxylate anionic surfactants alone or phosphate anionic surfactants alone may not be fully responsive to the differing coloration demands of the roots and tips of hair strands. It is believed that the mixture of two phosphate surfactants in combination with their fatty alcohol antecedent, the nonionic surfactant and the viscosity control compound without inclusion of a fatty acid and fatty acid ester at least in part facilitates the responsive coloration from roots to tips.

Packaging

In an embodiment of the presently claimed invention, before use, the tint and oxidizer composition components are normally packaged separately from one another. These composition components may be packaged in separate primary packages such as plastic bottle, sachet or tube. The components, in particular each component of a two-component composition, may however be packaged separately but within a common secondary package such as a carton or in different compartment of an aerosol or foam bottle, as is known in the trade. A conditioning composition, which can be applied after rinsing of the oxidative hair coloring composition, may also be packaged in such a secondary package. On the other hand, the different components of embodiments of the invention such as the third component, may be sold separately from the other components.

Method of Hair Dying

Embodiments of the method for application of the oxidative hair coloring composition to the hair may be undertaken in several ways. Application of the oxidative hair coloring composition may take place on the whole head of hair of an end user. As used herein, the "whole head of hair" means that the hair all over the head from the root of the hair to the tip of the hair is included in the application process.

Alternatively, the application of the oxidative hair coloring composition may take place only on the root portion of the hair. The application to the root portion of the hair may still be over the entire head of the end user, but application of the oxidative hair coloring composition only to the section of hair closest to the head (root portion) is performed on sections between about 0.01 mm to about 40 mm from the scalp of the head. After application to the root portion, product may be applied to the rest of the hair at a later stage to prevent over processing of the hair in the lengths and ends.

Also, application may take place on a portion of hair, application of a portion of hair is commonly referred to as highlighting or lowlighting. The portion of hair may be physically separated as a hair bundle from the whole head of hair or may be a smaller portion of hair than the whole head of hair i.e. a swatch. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in an additional container. In the latter case, the conditioner can be mixed immediately before use and applied together with the other components, or preferably the content of the additional container can be applied (after an optional rinse step) as a post-treatment immediately after the oxidative hair coloring composition.

According to one method for oxidatively coloring hair, the method comprises mixing embodiments of the tint composition and the oxidizer composition components together to form the oxidative hair coloring composition, applying the oxidative hair coloring composition to the hair either as a whole head of hair, or preferably to hair bundles or to swatches to develop pseudo-resorcinol control of the color progression in the negative L* direction over a period of 20 to 30 minutes after the last swatch or bundle or last part of the whole head of hair is treated and then removing the oxidative hair coloring composition from all treated hair swatches or bundles or whole head of hair by thorough rinsing with water.

The methods of coloring hair also may further comprise working the oxidative hair coloring composition into the treated hair surface by hand or by a tool for a few minutes to ensure uniform application to the entire treated hair surface. According to embodiments of the method of the invention, the oxidative hair coloring composition is applied to the hair and the pseudo-resorcinol control of color progression over a time period of about 20 to 30 minutes occurs. The consumer or salon professional then at her/his leisure rinses the oxidatively colored hair thoroughly with tap water and allows it to dry and/or styles the oxidatively colored hair.

In one embodiment of the presently claimed invention, a method of treating hair with the oxidative hair coloring composition preferably comprises the steps of:

a. providing a tint composition component as described herein;
b. providing an oxidizer composition component as described herein;
c. mixing the oxidizing composition and the tint composition to obtain an oxidative hair coloring composition as described herein;
d. applying the oxidative hair coloring composition for the oxidative dyeing of keratin fibres onto the hair;
e. leaving the composition on the hair for at least 20 to 30 minutes or longer; and
f. subsequently rinsing the oxidative hair coloring composition from the hair.

In one embodiment of the presently claimed invention, the oxidative hair coloring composition may be obtained by mixing immediately prior to use a tint composition and the oxidizing composition. A sufficient amount of the resulting oxidative hair coloring composition is applied to the hair, according to the hair abundance, generally from 20 to 250 grams depending on the amount of hair to be colored. Upon such preparation, the oxidative hair coloring composition is applied to the hair to be dyed and remains in contact with the hair for an amount of time effective to dye the hair. Typically, the oxidative hair coloring composition is allowed to act on the hair at least for 20 to 30 minutes, at a temperature ranging from 15 to 23° C. Thereafter, the hair is rinsed with water to remove excess oxidative hair coloring composition as well as residues and dried. If necessary, the hair is washed with a shampoo and rinsed, e.g., with water or a weakly acidic solution, such as a citric acid or tartaric acid solution, and dried. Optionally, a separate conditioning product may also be provided.

The oxidative hair coloring composition can be applied on hair via an applicator bottle or brush. It can be used on full head or partly on single strands (highlight application) as common highlight applicator foils, caps and special applicators can be used, but also freehand techniques such as balayage, with brush and/or combs can be possible. The oxidative hair coloring composition can also be applied as a mousse via a manual spray, a pressurized container or an aerosol mousse. The oxidative hair coloring composition may be dispensed as a solid form to which water is added to generate the oxidant and form a thickened vehicle suitable for hair coloring.

EXAMPLES

The following examples illustrate the formulations and performance results of embodiments of methods utilizing embodiments of the oxidative hair coloring composition. These examples are not intended to be inclusive of all aspects of the subject matter disclosed herein, but rather to illustrate representative compositions and results. These examples are not intended to exclude equivalents and variations of the presently claimed invention, which are apparent to one skilled in the art.

Hair Tresses (Swatches) Used for Testing.

The tresses may be subjected to the following color treatments to reflect consumers lengths and end hair. Natural white undamaged human hair (NW hair) is purchased (Kerling International Haarfabrik GmbH, Backnang, Germany) in the form of 10 cm long and 1 cm wide tresses. G3 level grey hair mixed with medium brown hair is purchased from a supplier source in Italy.

Method of Applying Hair Coloring Formulation to Hair

All products and equipment for the hair dye-out may be equilibrated to 30° C. in a circulation oven overnight. Equal weights (approximately 4 g each) of tint composition and oxidizing composition may be mixed in a plastic bowl using a dye-out brush. This mixture is referred to as the oxidative hair coloring composition (with glycine and no resorcinol) for embodiments of the invention and as several altered versions of the oxidative hair dye composition (one with no resorcinol and no glycine, one with resorcinol and no glycine, one with both of resorcinol and glycine as the test compositions).

The hair tress may be placed on a plastic plate and about 2 gm of the oxidative hair coloring composition or test compositions may be applied to the free hair portion of a tress and the color developed at 30° C. for periods of 10, 20, 25 and 30 minutes in a 30° C. air circulation oven. After color development period and removal from the oven, excess oxidative hair coloring composition or test compositions may be squeezed out from the tress by hand, wearing nitrile gloves and the tress washed in 4 L min water at 37 C for 2 min. The hair may be then blow dried.

The L* value (lightness-darkness value), a* (green to red component value) and b* (blue to yellow component value) of hair swatches colored with the oxidative hair coloring hair coloring composition and with the test compositions may be measured using a Minolta 2600d spectrophotometer.

For each tress, ten measurements may be taken, five on each side of the tress. The error analysis may be done using standard statistical formulae and functions in Microsoft Excel.

Ingredient Formulas for Coloring the Hair Tresses (Swatches)

The formulas of the test compositions (TC) are prepared according to the following method. The test compositions are:

(1) the test composition TC-1 which is the oxidative hair coloring composition but does not contain glycine nor resorcinol,
(2) the TC-2 (TC-1 with resorcinol but no glycine),
(3) the TC-3 (TC-1 with resorcinol and glycine), and
(4) TC-4, the oxidative hair coloring composition (TC-1 with glycine).

A chassis premix formula may be used for the tint formulation and the oxidizing formulation. Components of the chassis premix formula that would undergo oxidation and that are incompatible with the oxidizing formulation are to be omitted when used as a chassis for the oxidizing formulation.

The chassis premix formula is prepared from the ingredients and concentrations given in Table I.

Table II provides the Shade 2N to Shade 5N list of and concentrations of the precursors and couplers for forming the final 2N to 5N TC compositions (1) through (4) above. The chassis premix formula of Table I is combined with precursors and couplers of Table II to form the Shade 2N through Shade 5N TC compositions (1) through (4). The alkalizers, ascorbic acid, and thickeners of the premix formula are omitted when used with the oxidizing formulation, and phosphoric acid, sodium phosphate and pyrophosphate and etidronic acid are included.

Table III provides a summary of the Shade 2N through Shade 5N compositions for (1) TC-1 without glycine and without resorcinol, (2) TC-2 with resorcinol, (3) TC-3 with resorcinol and glycine and (4) the oxidative hair coloring composition, TC-4 with glycine.

Table IV shows the total precursor and coupler concentrations for Shades 2N through 5N. Table IV illustrates that these concentrations decrease from Shade 2N (largest totals of precursor and coupler concentrations) to Shade 5N (lowest totals of precursor and coupler concentrations). Concentration of precursor total without resorcinol is lower from 2N to 5N than is the concentration of precursor total with resorcinol from 2N to 5N. The coupler total for the TC-2 with resorcinol is always larger than the corresponding coupler total for TC-1 without resorcinol. The comparisons of coupler and precursor totals show that the totals for both are larger with resorcinol than without resorcinol. This variation results from addition of a resorcinol concentration to the existing couplers of the TC-1. It also necessitates an increase in the total precursor concentration.

TABLE I

| Chassis | |
|---|---|
| Chassis Description for all shades 2N, 3N, 4N, 5N | wt % relative to total composition |
| Water Purified, USP, JSQI | 62-69 wt %, depending on concentrations of precursor(s) and coupler(s) |
| Cetearyl Alcohol | about 6-7% |
| Dicetyl Phosphate AND Ceteth-10 Phosphate | about 1.5-2.25% |
| Steareth-200 | about 0.5-1.5% |
| Propylene Glycol (Pharma or Cosmetic Grade) | about 8- 9% |
| Xanthan Gum | about 0.1-0.2% |
| Sodium Hydroxide (beads) | about 2-3% |
| Trisodium Ethylenediamine Disuccinate | about 0.2-1.2% |
| Ascorbic acid | about 0.1-0.5% |
| Disodium EDTA | about 0.05-0.15% |
| Sodium Sulfite anhydrous | about 0.2-0.8% |
| Ammonium Carbonate | about 4-6% |
| SHEER AMETHYST | about 0.2-0.3% |

TABLE II

| Precursor and Couplers for Shades 2N through 5N (~=about) | | | | | | | | |
|---|---|---|---|---|---|---|---|---|
| Precursor/Coupler | Shade 2N no R | Shade 2N with R | Shade 3N no R | Shade 3N with R | Shade 4N no R | Shade 4N with R | Shade 5N no R | Shade 5N with R |
| 2-METHOXYMETHYL-P-PHENYLENEDIAMINE precursor | ~2.3-2.4% | ~3.2-3.3% | ~1.8-1.9% | ~2.8-2.9% | ~1.6-1.7% | ~2.0-2.1% | ~1.5-1.6% | ~2.1-2.2% |
| P-AMINOPHENOL precursor | | | | | | | ~0.2-0.3% | ~0.2-0.3% |
| 1-HEXYL 4,5-DIAMINO PYRAZOLE SULFATE, precursor | | ~0.06-0.07% | | | | | | |
| 2,4-DIAMINOPHENOXY ETHANOL HCL coupler | ~1.08-1.09% | ~1.4-1.5% | ~0.8-0.9% | ~0.9-1.9% | ~0.3-0.4% | ~0.4-0.5% | ~0.1-0.15% | ~0.1-0.2% |
| HYDROXYETHYL-3,4-METHYLENEDIOXY ANILINE HCL (Aminol) coupler | ~1.0-1.1% | ~1.0-1.1% | ~0.8-0.9% | ~0.8-0.9% | ~0.8-0.9% | ~0.8-0.9% | ~0.9-1.0% | ~1.0-1.1% |
| 4-Amino-2-Hydroxytoluene, coupler | ~0.1-0.15% | ~0.03-0.04% | 0.15% | ~0.1-0.2% | ~0.05-0.1% | ~0.2-0.15% | ~0.1-0.2% | ~0.1-0.2% |
| M-AMINOPHENOL, coupler | ~0.3-0.4% | ~0.2-0.3% | ~0.2-0.3% | ~0.2-0.3% | ~0.2-0.3% | none | ~0.3-0.4% | ~0.7-0.8% |
| EthylOAP, coupler | | | | | ~0.2-0.25% | | | |
| Resorcinol | none | ~0.90% | none | ~0.79% | none | ~0.70% + ~0.39% of 2MeR | none | ~0.70% |

TABLE III

| Breakdown of Shades 2N-5N according to TC's 1-4 | | | | | | | | | | | | | | | | |
|---|---|---|---|---|---|---|---|---|---|---|---|---|---|---|---|---|
| | Shade 2N No Resorcinol | | Shade 2N Resorcinol | | Shade 3N No Resorcinol | | Shade 3N Resorcinol | | Shade 4N No Resorcinol | | Shade 4N Resorcinol | | Shade 5N No Resorcinol | | Shade 5N Resorcinol | |
| With or W/O Glycine (wt %) | 3.36 | none | 3.36 | none | 3.36 | none | 3.36 | none | 3.36 | none | 3.36 | none | 3.36 | none | 3.36 | none |
| Compositions 2N-5N | TC4 | TC1 | TC3 | TC2 | TC4 | TC1 | TC3 | TC2 | TC4 | TC1 | TC3 | TC2 | TC4 | TC1 | TC3 | TC2 |

TABLE IV

| Precursor and Coupler Concentrations 2N to 5N TC-1 and TC-2 | | | | | | | | |
|---|---|---|---|---|---|---|---|---|
| Shade, R = resorcinol | 2N no R OHDC 1 | 2N w R OHDC 2 | 3N no R OHDC 1 | 3N with R OHDC2 | 4N no R OHDC1 | 4N with R OHDC2 | 5N no R OHDC1 | 5N with R OHDC2 |
| Precursor totals | about 2.2-2.5% | about 3-4% | about 1.7-2.2% | about 2.5-3.2% | about 1.5-2% | about 1.8-2.1% | about 1.6-2.0% | about 2.1-2.5% |
| Coupler totals | about 2.4-2.8% | about 3.5-4.0% | about 2.0-2.4% | about 3.0-3.3% | about 1.5-1.9% | about 2.2-2.7% | about 1.4-1.8% | about 2.0-2.4% |
| W or W/O Resorcinol | W/O | W | W/O | W | W/O | W | W/O | W |

Pursuant to the hair swatch color treatment procedure described above, G3 hair swatches are prepared with each of the Shades 2N through 5N TC's 1-4: (1) the oxidative hair dyeing composition without resorcinol nor glycine (TC-1), (2) the TC-2 with resorcinol, (3) the TC-3 with resorcinol and glycine and (4) TC-4 the oxidative hair coloring composition with glycine. G3 hair swatches are 50% blended grey hair with Natural level 3 medium brown hair. The Natural hair color scale ranges from Natural level 1 as black to Natural level 3 as medium brown to Natural level 8 as blonde. Use of the G3 swatches indicates how well mixed grey hair will be covered by the hair color.

The colors of the resulting hair swatches are examined by the Minolta procedure given above to determine the L*a*b* color space provided by the Oxidative hair coloring composition and the comparative resorcinol composition. These results are provided on the following Tables V—2N, V-3N, V-4N and V-5N for each of the four TC's wherein with R means with Resorcinol, W/O R means without Resorcinol, with G means with Glycine, W/O G means without Glycine, W/O R, W/O G means without Resorcinol and without Glycine.

The L*ab numbers of the Tables VI 2N-5N run from 20-14 for L, 4.18 to 0.08 for a and 5.27 to −0.75 for b. All of these numbers indicate a black color visually. The shade is the "blackness" of this black color. For example, an L*ab of 20.09, 3.62 and 4.27 for 5N with resorcinol, (the lowest concentrations of precursors and couplers of the 2N to 5N Shades) is industrial black, also known as granite brown. If the L* is raised to 50, the color is brown also known as teakwood brown. If L* is raised to 75, the color is beige also known as taupe. If L* is raised to 90, the color is sable wood, also known as faint coral. If L* is raised to 99, the color is off-white with a slight rose hint. These visual colors based on the CIELAB scale can be seen using the e-paint color conversion of L*a*b* to nearest standard color, see http://www.e-paint.co.uk/convert-lab-asp.

Visually, all of the colors of 2N-5N are dark brown to black. By eye, these shades do not appear different. Use of a spectrometer provides a spectrograph representation of the degree of "blackness" of this dark brown color. The progression of the degree of blackness is shown by the decreasing L* value at 10, 20, 25 and 30 minutes. For example, the 2N TC-1 reading at 10 minutes is characterized by e-paint as slate black and at 20 minutes the reading is characterized by e-paint as ink black. The visual color representation of these two colors on the e-paint site is black.

TABLE V

| Shade 2N | | | |
|---|---|---|---|
| Shade 2N, With R, With G | L*(D65) | a*(D65) | b*(D65) |
| 2N with resorcinol and Glycine-10 min | 15.88 | 0.23 | −0.56 |
| 2N with resorcinol and Glycine-20 min | 15.3 | 0.19 | −0.1 |
| 2N with resorcinol and Glycine-25 min | 14.91 | 0.16 | −0.11 |
| 2N with resorcinol and Glycine-30 min | 14.88 | 0.12 | −0.12 |
| Shade 2N, With R, W/O G | L*(D65) | a*(D65) | b*(D65) |
| 2N with resorcinol, w/o Glycine-10 min | 15.51 | 0.23 | −0.51 |
| 2N with resorcinol, w/o Glycine-20 min | 14.74 | 0.13 | −0.17 |
| 2N with resorcinol, w/o Glycine-25 min | 15.03 | 0.08 | −0.18 |
| 2N with resorcinol, w/o Glycine-30 min | 15.03 | 0.12 | −0.14 |
| Shade 2N, W/O R, With G | L*(D65) | a*(D65) | b*(D65) |
| 2N w/o resorcinol, with Glycine-10 min | 15 | 0.29 | −0.56 |
| 2N w/o resorcinol, with Glycine-20 min | 14.79 | 0.25 | −0.2 |

TABLE V-continued

| Shade 2N | | | |
|---|---|---|---|
| 2N w/o resorcinol, with Glycine-25 min | 14.86 | 0.31 | −0.13 |
| 2N w/o resorcinol, with Glycine-30 min | 15.7 | 0.27 | −0.19 |
| Shade 2N, W/O R, W/O G | L*(D65) | a*(D65) | b*(D65) |
| 2N w/o resorcinol and Glycine-10 min | 16.11 | 0.26 | −0.43 |
| 2N w/o resorcinol and Glycine-20 min | 14.78 | 0.15 | −0.21 |
| 2N w/o resorcinol and Glycine-25 min | 15.11 | 0.18 | −0.18 |
| 2N w/o resorcinol and Glycine-30 min | 14.24 | 0.23 | −0.14 |

TABLE V

| Shade 3N | | | |
|---|---|---|---|
| Shade 3N, With R, With G | L*(D65) | a*(D65) | b*(D65) |
| 3N with resorcinol and Glycine-10 min | 15.39 | 0.31 | −0.35 |
| 3N with resorcinol and Glycine-20 min | 14.45 | 0.2 | −0.15 |
| 3N with resorcinol and Glycine-25 min | 14.8 | 0.2 | −0.1 |
| 3N with resorcinol and Glycine-30 min | 14.71 | 0.25 | −0.07 |
| Shade 3N, With R, W/O G | L*(D65) | a*(D65) | b*(D65) |
| 3N with resorcinol, w/o Glycine-10 min | 15.49 | 0.27 | −0.4 |
| 3N with resorcinol, w/o Glycine-20 min | 14.7 | 0.25 | −0.04 |
| 3N with resorcinol, w/o Glycine-25 min | 14.99 | 0.17 | −0.1 |
| 3N with resorcinol, w/o Glycine-30 min | 14.9 | 0.14 | −0.13 |
| Shade 3N, W/O R, With G | L*(D65) | a*(D65) | b*(D65) |
| 3N w/o resorcinol, with Glycine-10 min | 15.68 | 0.38 | −0.61 |
| 3N w/o resorcinol, with Glycine-20 min | 15.41 | 0.29 | −0.26 |
| 3N w/o resorcinol, with Glycine-25 min | 15.34 | 0.35 | −0.12 |
| 3N w/o resorcinol, with Glycine-30 min | 14.59 | 0.27 | −0.13 |
| Shade 3N, W/O R, W/O G | L*(D65) | a*(D65) | b*(D65) |
| 3N w/o resorcinol and Glycine-10 min | 16.25 | 0.52 | −0.75 |
| 3N w/o resorcinol and Glycine-20 min | 15.1 | 0.23 | −0.21 |
| 3N w/o resorcinol and Glycine-25 min | 14.66 | 0.2 | −0.13 |
| 3N w/o resorcinol and Glycine-30 min | 14.45 | 0.25 | −0.07 |

TABLE V

| Shade 4N | | | |
|---|---|---|---|
| Shade 4N, With R, With G | L*(D65) | a*(D65) | b*(D65) |
| 4N with resorcinol and Glycine-10 min | 19.18 | 1.03 | 0.95 |
| 4N with resorcinol and Glycine-20 min | 16.92 | 0.81 | 0.92 |
| 4N with resorcinol and Glycine-25 min | 16.44 | 0.88 | 1.06 |
| 4N with resorcinol and Glycine-30 min | 15.27 | 0.75 | 0.88 |
| Shade 4N, With R, W/O G | L*(D65) | a*(D65) | b*(D65) |
| 4N with resorcinol, w/o Glycine-10 min | 19.59 | 1.35 | 1.13 |
| 4N with resorcinol, w/o Glycine-20 min | 16.58 | 0.84 | 0.9 |
| 4N with resorcinol, w/o Glycine-25 min | 15.67 | 0.68 | 0.73 |
| 4N with resorcinol, w/o Glycine-30 min | 14.8 | 0.6 | 0.68 |
| Shade 4N, W/O R, With G | L*(D65) | a*(D65) | b*(D65) |
| 4N w/o resorcinol, with Glycine-10 min | 18.88 | 0.86 | 1 |
| 4N w/o resorcinol, with Glycine-20 min | 17.23 | 0.81 | 0.83 |
| 4N w/o resorcinol, with Glycine-25 min | 16.81 | 0.87 | 0.84 |
| 4N w/o resorcinol, with Glycine-30 min | 15.86 | 0.72 | 0.61 |
| Shade 4N, W/O R, W/O G | L*(D65) | a*(D65) | b*(D65) |
| 4N w/o resorcinol and Glycine-10 min | 18.18 | 1.19 | 1.21 |
| 4N w/o resorcinol and Glycine-20 min | 16.12 | 0.69 | 0.85 |
| 4N w/o resorcinol and Glycine-25 min | 15.25 | 0.61 | 0.83 |
| 4N w/o resorcinol and Glycine-30 min | 15.29 | 0.57 | 0.63 |

TABLE V

| Shade 5N | | | |
|---|---|---|---|
| Shade Name 5N, With R, With G | L*(D65) | a*(D65) | b*(D65) |
| 5N With Resorcinol and Glycine 10 min | 20.09 | 3.62 | 5.27 |
| 5N With Resorcinol and Glycine 20 min | 16.29 | 2.28 | 2.29 |
| 5N With Resorcinol and glycine 25 min | 15.69 | 2.3 | 1.98 |
| 5N With Resorcinol and Glycine 30 min | 16.08 | 2.24 | 1.67 |
| Shade 5N, W/O R, With G | L*(D65) | a*(D65) | b*(D65) |
| 5N W/O Resorcinol with Glycine 10 min | 20.04 | 3.47 | 5.04 |
| 5N W/O Resorcinol with Glycine 20 min | 17.42 | 2.68 | 2.59 |
| 5N W/O Resorcinol with Glycine 25 min | 16.63 | 2.77 | 2.47 |
| 5N W/O Resorcinol with Glycine 30 min | 16.84 | 2.69 | 2.48 |
| Shade 5N, W/O R, W/O G | L*(D65) | a*(D65) | b*(D65) |
| 5N 10 min without Resorcinol and Glycine | 19.49 | 4.18 | 5.26 |
| 5N 20 min without Resorcinol and Glycine | 17.02 | 2.37 | 2.24 |
| 5N 25 min without Resorcinol and Glycine | 16.34 | 2.39 | 1.92 |

TABLE V-continued

| Shade 5N | | | |
|---|---|---|---|
| 5N 30 min without Resorcinol and Glycine | 16.26 | 2.13 | 1.6 |
| Shade 5N, With R, W/O G | L*(D65) | a*(D65) | b*(D65) |
| 5N 10 min with Resorcinol without Glycine | 18.33 | 3.2 | 3.86 |
| 5N 20 min with Resorcinol without Glycine | 15.15 | 1.73 | 1.43 |
| 5N 25 min with Resorcinol without Glycine | 15.89 | 1.62 | 1.24 |
| 5N 30 min with Resorcinol without Glycine | 15.89 | 1.51 | 1.07 |

The Shade Spectra of Shade Tables 2N-5N are compared in the following Tables according to the scheme: compare TC-1 with TC-2; compare TC-2 with TC-3; compare TC-2 with TC-4 and compare TC-1 with TC-4. TC is the acronym for test composition which is an embodiment of the oxidative hair coloring composition according to the invention but without glycine. The numbers after TC indicate without glycine and without resorcinol (TC-1), with resorcinol (TC-2), with resorcinol and glycine (TC-3), with glycine (TC-4). The numbers 1, 2, 3, 4 also indicate the presence or absence of resorcinol and glycine in the 2N-5N Shade numbers described below.

TABLE VI

2N COMPARISONS
2N Test Compositions (TC-1 through TC-4) showing pseudo-resorcinol action or lack of such action for these Four different 2N Formulations where the concentrations of the precursors and couplers for these 2N TC's are as shown on Table II:
2N-1 Without Resorcinol, Without Glycine (2N TC-1)
2N-2 With Resorcinol, Without Glycine (2N TC-2)
2N-3 With Resorcinol, With Glycine (2N TC-3)
2N-4 Without Resorcinol, With Glycine (2N TC-4).

| 2N-1 versus 2N-2 | | | | | | | |
|---|---|---|---|---|---|---|---|
| 2N-1, W/O R, W/O G | L*(D65) | a*(D65) | b*(D65) | 2N-2, W R, W/O G | L*(D65) | a*(D65) | b*(D65) |
| 2N-1, W/O R, W/O G-10 min | 16.11 | 0.26 | −0.43 | 2N-2, W R, W/O G-10 min | 15.51 | 0.23 | −0.51 |
| 2N-1, W/O R, W/O G-20 min | 14.78 | 0.15 | −0.21 | 2N-2, W R, W/O G-20 min | 14.74 | 0.13 | −0.17 |
| 2N-1, W/O R, W/O G-25 min | 15.11 | 0.18 | −0.18 | 2N-2, W R, W/O G-25 min | 15.03 | 0.08 | −0.18 |
| 2N-2 versus 2N-3 | | | | | | | |
| 2N-2, W R, W/O G | L*(D65) | a*(D65) | b*(D65) | 2N-3, W R, W G | L*(D65) | a*(D65) | b*(D65) |
| 2N-2, W R, W/O G-10 min | 15.51 | 0.23 | −0.51 | 2N-3, W R, W G-10 min | 15.88 | 0.23 | −0.56 |
| 2N-2, W R, W/O G-20 min | 14.74 | 0.13 | −0.17 | 2N-3, W R, W G-20 min | 15.3 | 0.19 | −0.1 |
| 2N-2, W R, W/O G-25 min | 15.03 | 0.08 | −0.18 | 2N-3, W R, W G-25 min | 14.91 | 0.16 | −0.11 |
| 2N-2, W R, W/O G-30 min | 15.03 | 0.12 | −0.14 | 2N-3, W R, W G-30 min | 14.88 | 0.12 | −0.12 |
| 2N-2 versus 2N-4 | | | | | | | |
| 2N-2, W R, W/O G | L*(D65) | a*(D65) | b*(D65) | 2N-4, W/O R, W G | L*(D65) | a*(D65) | b*(D65) |
| 2N-2, W R, W/O G-10 min | 15.51 | 0.23 | −0.51 | 2N-4, W/O R, W G-10 min | 15 | 0.29 | −0.56 |
| 2N-2, W R, W/O G-20 min | 14.74 | 0.13 | −0.17 | 2N-4, W/O R, W G-20 min | 14.79 | 0.25 | −0.2 |
| 2N-2, W R, W/O G-25 min | 15.03 | 0.08 | −0.18 | 2N-4, W/O R, W G-25 min | 14.86 | 0.31 | −0.13 |
| 2N-2, W R, W/O G-30 min | 15.03 | 0.12 | −0.14 | 2N-4, W/O R, W G-30 min | 15.7 | 0.27 | −0.19 |

TABLE VI-continued

2N COMPARISONS
2N Test Compositions (TC-1 through TC-4) showing pseudo-resorcinol action or lack of such action for these Four different 2N Formulations where the concentrations of the precursors and couplers for these 2N TC's are as shown on Table II:
2N-1 Without Resorcinol, Without Glycine (2N TC-1)
2N-2 With Resorcinol, Without Glycine (2N TC-2)
2N-3 With Resorcinol, With Glycine (2N TC-3)
2N-4 Without Resorcinol, With Glycine (2N TC-4).

2N-1 versus 2N-4

| 2N-1, W/O R, W/O G | L*(D65) | a*(D65) | b*(D65) | 2N-4, W/O R, W G | L*(D65) | a*(D65) | b*(D65) |
|---|---|---|---|---|---|---|---|
| 2N-1, W/O R, W/O G-10 min | 16.11 | 0.26 | −0.43 | 2N-4, W/O R, W G-10 min | 15 | 0.29 | −0.56 |
| 2N-1, W/O R, W/O G-20 min | 14.78 | 0.15 | −0.21 | 2N-4, W/O R, W G-20 min | 14.79 | 0.25 | −0.2 |
| 2N-1, W/O R, W/O G-25 min | 15.11 | 0.18 | −0.18 | 2N-4, W/O R, W G-25 min | 14.86 | 0.31 | −0.13 |
| 2N-1, W/O R, W/O G-30 min | 14.24 | 0.23 | −0.14 | 2N-4, W/O R, W G-30 min | 15.7 | 0.27 | −0.19 |

TABLE VI

3N COMPARISONS
3N Test Compositions (TC-1 through TC-4), showing pseudo-resorcinol action or lack of such action for these Four different 3N Formulations where the concentrations of the precursors and couplers for these 3N TC's are as shown on Table II:
3N-1Without Resorcinol, Without Glycine (3N-1, WR, W/O G)
3N-2 With Resorcinol, Without Glycine (3N-2, WR, W/O G
3N-3 With Resorcinol, With Glycine (3N-3, WR, W G)
3N-4 Without Resorcinol, With Glycine (3N-4 W/OR, W G).

3N-1 versus 3N-2

| 3N-1, W/O R, W/O G | L*(D65) | a*(D65) | b*(D65) | 3N-2, W R, W/O G | L*(D65) | a*(D65) | b*(D65) |
|---|---|---|---|---|---|---|---|
| 3N-1, W/O R, W/O G-10 min | 16.25 | 0.52 | −0.75 | 3N-2, W R, W/O G-10 min | 15.49 | 0.27 | −0.4 |
| 3N-1, W/O R, W/O G-20 min | 15.1 | 0.23 | −0.21 | 3N-2, W R, W/O G-20 min | 14.7 | 0.25 | −0.04 |
| 3N-1, W/O R, W/O G-25 min | 14.66 | 0.2 | −0.13 | 3N-2, W R, W/O G-25 mir | 14.99 | 0.17 | −0.1 |
| 3N-1, W/O R, W/O G-30 min | 14.45 | 0.25 | −0.07 | 3N-2, W R, W/O G-30 min | 14.90 | 0.14 | −0.13 |

3N-2 versus 3N-3

| 3N-2, W R, W/O G | L*(D65) | a*(D65) | b*(D65) | 3N-3, W R, W G | L*(D65) | a*(D65) | b*(D65) |
|---|---|---|---|---|---|---|---|
| 3N-2, W R, W/O G-10 min | 15.49 | 0.27 | −0.4 | 3N-3, W R, W G-10 min | 15.39 | 0.31 | −0.35 |
| 3N-2, W R, W/O G-20 min | 14.7 | 0.25 | −0.04 | 3N-3, W R, W G-20 min | 14.45 | 0.2 | −0.15 |
| 3N-2, W R, W/O G-25 min | 14.99 | 0.17 | −0.1 | 3N-3, W R, W G-25 min | 14.8 | 0.2 | −0.1 |
| 3N-2, W R, W/O G-30 min | 14.90 | 0.14 | −0.13 | 3N-3, W R, W G-30 min | 14.71 | 0.25 | −0.07 |

TABLE VI-continued

3N COMPARISONS
3N Test Compositions (TC-1 through TC-4), showing pseudo-resorcinol action or lack of such action for these Four different 3N Formulations where the concentrations of the precursors and couplers for these 3N TC's are as shown on Table II:
3N-1Without Resorcinol, Without Glycine (3N-1, WR, W/O G)
3N-2 With Resorcinol, Without Glycine (3N-2, WR, W/O G
3N-3 With Resorcinol, With Glycine (3N-3, WR, W G)
3N-4 Without Resorcinol, With Glycine (3N-4 W/OR, W G).

3N-2 versus 3N-4

| 3N-2, W R, W/O G | L*(D65) | a*(D65) | b*(D65) | 3N-4, W/O R, W G | L*(D 65) | a*(D65) | b*(D65) |
|---|---|---|---|---|---|---|---|
| 3N-2, W R, W/O G-10 min | 15.49 | 0.27 | −0.4 | 3N-4, W/O R, W G-10 min | 15.68 | 0.38 | −0.61 |
| 3N-2, W R, W/O G-20 min | 14.7 | 0.25 | −0.04 | 3N-4, W/O R, W G-20 min | 15.41 | 0.29 | −0.26 |
| 3N-2, W R, W/O G-25 min | 14.99 | 0.17 | −0.1 | 3N-4, W/O R, W G-25 min | 15.34 | 0.35 | −0.12 |
| 3N-2, W R, W/O G-30 min | 14.90 | 0.14 | −0.13 | 3N-4, W/O R, W G-30 min | 14.59 | 0.27 | −0.13 |

3N-1 versus 3N-4

| 3N-1, W/O R, W/O G | L*(D65) | a*(D65) | b*(D65) | 3N-4, W/O R, W G | L*(D65) | a*(D65) | b*(D65) |
|---|---|---|---|---|---|---|---|
| 3N-1, W/O R, W/O G-10 min | 16.25 | 0.52 | −0.75 | 3N-4, W/O R, W G-10 min | 15.68 | 0.38 | −0.61 |
| 3N-1, W/O R, W/O G-20 min | 15.1 | 0.23 | −0.21 | 3N-4, W/O R, W G-20 min | 15.41 | 0.29 | −0.26 |
| 3N-1, W/O R, W/O G-25 min | 14.66 | 0.2 | −0.13 | 3N-4, W/O R, W G-25 min | 15.34 | 0.35 | −0.12 |
| 3N-1, W/O R, W/O G-30 min | 14.45 | 0.25 | −0.07 | 3N-4, W/O R, W G-30 min | 14.59 | 0.27 | −0.13 |

TABLE VI

4N COMPARISONS
4N Test Compositions (TC-1 through TC-4), showing pseudo-resorcinol action or lack of such action for these Four different 4N Formulations where the concentrations of the precursors and couplers for these 4N TC's are as shown on Table II:
4N-1Without Resorcinol, Without Glycine (4N-1, WR, W/O G)
4N-2 With Resorcinol, Without Glycine (4N-2, WR, W/O G
4N-3 With Resorcinol, With Glycine (4N-3, WR, W G)
4N-4 Without Resorcinol, With Glycine (4N-4 W/OR, W G).

4N-1 versus 4N-2

| 4N-1, W/O R, W/O G | L*(D65) | a*(D65) | b*(D65) | 4N-2, W R, W/O G | L*(D65) | a*(D65) | b*(D65) |
|---|---|---|---|---|---|---|---|
| 4N-1, W/O R, W/O G-10 min | 18.18 | 1.19 | 1.21 | 4N-2, W R, W/O G-10 min | 19.59 | 1.35 | 1.13 |
| 4N-1, W/O R, W/O G-20 min | 16.12 | 0.69 | 0.85 | 4N-2, W R, W/O G-20 min | 16.58 | 0.84 | 0.9 |
| 4N-1, W/O R, W/O G-25 min | 15.25 | 0.61 | 0.83 | 4N-2, W R, W/O G-25 min | 15.67 | 0.68 | 0.73 |

TABLE VI-continued

| 4N COMPARISONS<br>4N Test Compositions (TC-1 through TC-4), showing pseudo-resorcinol action or lack of such action for these Four different 4N Formulations where the concentrations of the precursors and couplers for these 4N TC's are as shown on Table II:<br>4N-1Without Resorcinol, Without Glycine (4N-1, WR, W/O G)<br>4N-2 With Resorcinol, Without Glycine (4N-2, WR, W/O G<br>4N-3 With Resorcinol, With Glycine (4N-3, WR, W G)<br>4N-4 Without Resorcinol, With Glycine (4N-4 W/OR, W G). | | | | | | | |
|---|---|---|---|---|---|---|---|
| 4N-1, W/O R, W/O G-30 min | 15.29 | 0.57 | 0.63 | 4N-2, W R, W/O G-30 min | 14.8 | 0.6 | 0.68 |
| 4N-2 versus 4N-3 | | | | | | | |
| 4N-2, W R, W/O G | L*(D65) | a*(D65) | b*(D65) | 4N-3, W R, W G | L*(D65) | a*(D65) | b*(D65) |
| 4N-2, W R, W/O G-10 min | 19.59 | 1.35 | 1.13 | 4N-3, W R, W G-10 min | 19.18 | 1.03 | 0.95 |
| 4N-2, W R, W/O G-20 min | 16.58 | 0.84 | 0.9 | 4N-3, W R, W G-20 min | 16.92 | 0.81 | 0.92 |
| 4N-2, W R, W/O G-25 min | 15.67 | 0.68 | 0.73 | 4N-3, W R, W G-25 min | 16.44 | 0.88 | 1.06 |
| 4N-2, W R, W/O G-30 min | 14.8 | 0.6 | 0.68 | 4N-3, W R, W G-30 min | 15.27 | 0.75 | 0.88 |
| 4N-2 versus 4N-4 | | | | | | | |
| 4N-2, W R, W/O G | L*(D65) | a*(D65) | b*(D65) | 4N-4, W/O R, W G | L*(D65) | a*(D65) | b*(D65) |
| 4N-2, W R, W/O G-10 min | 19.59 | 1.35 | 1.13 | 4N-4, W/O R, W G-10 min | 18.88 | 0.86 | 1 |
| 4N-2, W R, W/O G-20 min | 16.58 | 0.84 | 0.9 | 4N-4, W/O R, W G-20 min | 17.23 | 0.81 | 0.83 |
| 4N-2, W R, W/O G-25 min | 15.67 | 0.68 | 0.73 | 4N-4, W/O R, W G-25 min | 16.81 | 0.87 | 0.84 |
| 4N-2, W R, W/O G-30 min | 14.8 | 0.6 | 0.68 | 4N-4, W/O R, W G-30 min | 15.86 | 0.72 | 0.61 |
| 4N-1 versus 4N-4 | | | | | | | |
| 4N-1, W/O R, W/O G | L*(D65) | a*(D65) | b*(D65) | 4N-4, W/O R, W G | L*(D65) | a*(D65) | b*(D65) |
| 4N-1, W/O R, W/O G-10 min | 18.18 | 1.19 | 1.21 | 4N-4, W/O R, W G-10 min | 18.88 | 0.86 | 1 |
| 4N-1, W/O R, W/O G-20 min | 16.12 | 0.69 | 0.85 | 4N-4, W/O R, W G-20 min | 17.23 | 0.81 | 0.83 |
| 4N-1, W/O R, W/O G-25 min | 15.25 | 0.61 | 0.83 | 4N-4, W/O R, W G-25 min | 16.81 | 0.87 | 0.84 |
| 4N-1, W/O R, W/O G-30 min | 15.29 | 0.57 | 0.63 | 4N-4, W/O R, W G-30 min | 15.86 | 0.72 | 0.61 |

TABLE VI

5N COMPARISONS
5N Test Compositions (TC-1 through TC-4), showing pseudo-resorcinol action or lack of such action for these Four different 5N Formulations where the concentrations of the precursors and couplers for these 5N TC's are as shown on Table II:
5N-1 Without Resorcinol, Without Glycine (5N-1, WR, W/O G)
5N-2 With Resorcinol, Without Glycine (5N-2, WR, W/O G
5N-3 With Resorcinol, With Glycine (5N-3, WR, W G)
5N-4 Without Resorcinol, With Glycine (5N-4 W/OR, W G).

| | | | | | | | |
|---|---|---|---|---|---|---|---|
| 5N-1 versus 5N-2 | | | | | | | |
| 5N-1, W/O R, W/O G | L*(D65) | a*(D65) | b*(D65) | 5N-2, W R, W/O G | L*(D65) | a*(D65) | b*(D65) |
| 5N-1, W/O R, W/O G 5N-10 min | 19.49 | 4.18 | 5.26 | 5N-2, W R, W/O G 10 min | 18.33 | 3.2 | 3.86 |
| 5N-1, W/O R, W/O G 5N-20 min | 17.02 | 2.37 | 2.24 | 5N-2, W R, W/O G 20 min | 15.15 | 1.73 | 1.43 |
| 5N-1, W/O R, W/O G 5N-25 min | 16.34 | 2.39 | 1.92 | 5N-2, W R, W/O G 25 min | 15.89 | 1.62 | 1.24 |
| 5N-1, W/O R, W/O G 5N-30 min | 16.26 | 2.13 | 1.6 | 5N-2, W R, W/O G 30 min | 15.89 | 1.51 | 1.07 |
| 5N-2 versus 5N-3 | | | | | | | |
| 5N-2, W R, W/O G | L*(D65) | a*(D65) | b*(D65) | 5N-3, W R, WG | L*(D65) | a*(D65) | b*(D65) |
| 5N-2, W R, W/O G 10 min | 18.33 | 3.2 | 3.86 | 5N-3, W R, W G 10 min | 20.09 | 3.62 | 5.27 |
| 5N-2, W R, W/O G 20 min | 15.15 | 1.73 | 1.43 | 5N-3, W R, W G 5N 20 min | 16.29 | 2.28 | 2.29 |
| 5N-2, W R, W/O G 25 min | 15.89 | 1.62 | 1.24 | 5N-3, W R, W G 5N 25 min | 15.69 | 2.3 | 1.98 |
| 5N-2, W R, W/O G 30 min | 15.89 | 1.51 | 1.07 | 5N-3, W R, W G 5N 30 min | 16.08 | 2.24 | 1.67 |
| 5N-2 versus 5N-4 | | | | | | | |
| 5N-2, W R, W/O G | L*(D65) | a*(D65) | b*(D65) | 5N-4, W/O R, W G | L*(D65) | a*(D65) | b*(D65) |
| 5N-2, W R, W/O G 10 min | 18.33 | 3.2 | 3.86 | 5N-4, W/O R, W G 10 min | 20.04 | 3.47 | 5.04 |
| 5N-2, W R, W/O G 20 min | 15.15 | 1.73 | 1.43 | 5N-4, W/O R, W G 20 min | 17.42 | 2.68 | 2.59 |
| 5N-2, W R, W/O G 25 min | 15.89 | 1.62 | 1.24 | 5N-4, W/O R, W G 25 min | 16.63 | 2.77 | 2.47 |
| 5N-2, W R, W/O G 30 min | 15.89 | 1.51 | 1.07 | 5N-4, W/O R, W G 30 min | 16.84 | 2.69 | 2.48 |
| 5N-1 versus 5N-4 | | | | | | | |
| 5N-1, W/O R, W/O G | L*(D65) | a*(D65) | b*(D65) | 5N-4, W/OR, WG | L*(D65) | a*(D65) | b*(D65) |
| 5N-1, W/O R, W/O G 5N-10 min | 19.49 | 4.18 | 5.26 | 5N-4, W/O R, W G 10 min | 20.04 | 3.47 | 5.04 |

TABLE VI-continued

5N COMPARISONS
5N Test Compositions (TC-1 through TC-4), showing pseudo-resorcinol action or lack of such action for these Four different 5N Formulations where the concentrations of the precursors and couplers for these 5N TC's are as shown on Table II:
5N-1 Without Resorcinol, Without Glycine (5N-1, WR, W/O G)
5N-2 With Resorcinol, Without Glycine (5N-2, WR, W/O G
5N-3 With Resorcinol, With Glycine (5N-3, WR, W G)
5N-4 Without Resorcinol, With Glycine (5N-4 W/OR, W G).

| | | | | | | | |
|---|---|---|---|---|---|---|---|
| 5N-1, W/O R, W/O G 5N-20 min | 17.02 | 2.37 | 2.24 | 5N-4, W/O R, W G 20 min | 17.42 | 2.68 | 2.59 |
| 5N-1, W/O R, W/O G 5N-25 min | 16.34 | 2.39 | 1.92 | 5N-4, W/O R, W G 25 min | 16.63 | 2.77 | 2.47 |
| 5N-1, W/O R, W/O G 5N-30 min | 16.26 | 2.13 | 1.6 | 5N-4, W/O R, W G 30 min | 16.84 | 2.69 | 2.48 |

The 2N comparison tables show:

a) The oxidative hair coloring composition without glycine and without resorcinol (2N-1, TC-1) continues to progress in the L* negative direction through 30 minutes while 2N-2 (TC-2, with resorcinol alone) shows a resorcinol control of the L* negative progression to a steady state at about 20 to 25 minutes.

b) Addition of glycine to 2N-2 (TC-3, with resorcinol and glycine) yields 2N-3 and inhibits the resorcinol control of L* negative progression so that the L* negative progression continues through 30 minutes.

c) 2N-4 (TC-4, with glycine alone) displays a pseudo-resorcinol control of the L* negative progression of L* like that displayed by 2N-2 (TC-2, resorcinol alone).

d) 2N-4 displays a pseudo-resorcinol control of L* negative progression compared with significant L* negative progression of 2N-1 (TC-1) throughout the 30 minute time period.

The 3N comparison tables show:

a) 3N-1(TC-1) continues to progress significantly in the L* negative direction through 30 minutes while the 3N-2 (TC-2) shows resorcinol control of the L* negative progression through about 30 minutes. This is the same as 2N-2.

b) Addition of glycine to the 3N-2 yields 3N-3 (TC-3) which shows no effect upon and no change upon the rate or extent of resorcinol action control of L*negative progression shown by 3N-2 over 30 minutes.

c) 3N-4 (TC-4) exhibits a pseudo-resorcinol control that is better and quicker than that displayed by 3N-2 (TC-2) in that the control reaches substantially a steady state faster than that reached by 3N2.

d) 3N-4 displays a pseudo-resorcinol control of L* progression through 30 minutes compared with the significant L* negative progression of 3N-1.

The 4N comparison tables show:

a) 4N-1 continues to progress significantly in the L* negative direction through 30 minutes while 4N-2 exhibits resorcinol control against the color progression in the L* negative direction. This difference occurs even though 4N-1 contains the coupler m-amino phenol while the 4N-2 instead contains 2-methyl resorcinol. 2-methyl resorcinol is a weaker coupler than resorcinol or m-amino phenol because of the steric hinderance of the methyls between the two hydroxyls.

b) Addition of glycine to 4N-2 yields 4N-3 (TC-3) which shows no effect upon and no change of the rate or extent of resorcinol control of L*negative progression shown by 4N-2 over 30 minutes.

c) Addition of glycine to 4N-1 yields 4N-4 (TC-4) which exhibits a pseudo-resorcinol control that is better and quicker than that displayed by 4N2 in that the control reaches substantially a steady state faster than that reached by 3N2.

d) 4N-4 (TC-4) displays a pseudo-resorcinol control of the negative L* progression through 30 minutes compared with the significant L* negative progression of 4N-1.

The 5N comparison tables show:

a) 5N-1 (TC-1) continues to darken significantly in the negative L* direction through 30 minutes while the 5N-2 (TC-2) shows a resorcinol control of the L* negative progression over about 30 minutes.

b) Addition of glycine to 5N-2 yields 5N-3 (TC-3 with resorcinol and glycine) which negatively affects L* negative progression shown by 5N-2 and does not provide a steep progression slope as 5N-2 indicating that glycine adversely affects, rather than affirmatively affects, the resorcinol action on 5N-2 L* progression.

c) Addition of glycine to 5N-1 to yield 5N-4 (TC-4) produces a pseudo-resorcinol control like that caused by 5N-2 (TC-2 resorcinol alone).

d) 5N-4 (TC-4) displays the pseudo-resorcinol control of the L* negative progression through 30 minutes compared with the significant L* negative progression of 5N-1.

These results demonstrate that the L* pseudo-resorcinol control of the TC-4 compositions 2N-4, 3N-4, 4N-4 and 5N-4 delivers an a*b* color space like that of the comparative resorcinol dye composition TC-2, 2N-2, 3N-2, 4N-2 and 5N-2 but the pseudo-resorcinol control of compositions TC-4, 2N-4, 3N-4, 4N-4 and 5N-4 avoids the environmental, health and toxic concerns of resorcinol and employs less precursor and coupler than does TC-2, 2N-2, 3N-2, 4N-2 and 5N-2. Moreover, these results demonstrate that addition of glycine and resorcinol to the test composition to provide TC-3 (Test Composition with resorcinol and glycine) lessens the resorcinol control of the L* negative progression. This shows that glycine does not enhance the resorcinol control of the L*negative progression but instead hinders and negates it.

The Pseudo-Resorcinol Control of the Color Progression of Oxidative Coloring Composition of the Invention The L* negative progression results are repeated for four 5N Shades encompassing embodiments of the test compositions: one with resorcinol and without glycine (5N-2), one with resorcinol and with glycine (5N-3), one without resorcinol and without glycine (5N-1), and one with glycine and without resorcinol (5N-4, embodiment of the oxidative hair coloring composition of the invention). Each Formulation was prepared as described above with the tint formula of shade 5N. The resorcinol and glycine additions and removals were as given. G3 hair tresses were used as the test hair material. Treatment of each tress was conducted as described above. The CIELAB spectrophotometer color results are presented in Tables VIA, VIB, VIC and VID.

TABLE VIA 5N-2 without glycine and with resorcinol

| KX 5N-2-W/o GLY, w/Res | L*(D65) | a*(D65) | b*(D65) |
|---|---|---|---|
| With Resorcinol 10 min | 18.33 | 3.2 | 3.86 |
| With Resorcinol 20 min | 15.15 | 1.73 | 1.43 |
| With Resorcinol 25 min | 15.89 | 1.62 | 1.24 |
| With Resorcinol 30 min | 15.89 | 1.51 | 1.07 |

TABLE VIB 5N-3 with glycine, with resorcinol

| KX-3 shade 5N | L*(D65) | a*(D65) | b*(D65) |
|---|---|---|---|
| With glycine, Resorcinol 10 min | 20.04 | 3.47 | 5.04 |
| with glycine, Resorcinol 20 min | 17.42 | 2.68 | 2.59 |
| with glycine, Resorcinol 25 min | 16.63 | 2.77 | 2.47 |
| With glycine, Resorcinol 30 min | 16.84 | 2.69 | 2.48 |

TABLE VIC 5N-1 without glycine without resorcinol

| KX 5N-1-W/o GLY, w/o Res | L*(D65) | a*(D65) | b*(D65) |
|---|---|---|---|
| Without Resorcinol 10 min | 19.49 | 4.18 | 5.26 |
| Without Resorcinol 20 min | 17.02 | 2.37 | 2.24 |
| Without Resorcinol 25 min | 16.34 | 2.39 | 1.92 |
| Without Resorcinol 30 min | 16.26 | 2.13 | 1.6 |

TABLE VID 5N-4 with glycine without resorcinol

| KX shade 5N-4 | L*(D65) | a*(D65) | b*(D65) |
|---|---|---|---|
| Without Resorcinol 10 min | 20.09 | 3.62 | 5.27 |
| Without Resorcinol 20 min | 16.29 | 2.28 | 2.29 |
| Without Resorcinol 25 min | 15.69 | 2.3 | 1.98 |
| Without Resorcinol 30 min | 16.08 | 2.24 | 1.67 |

5N-2 of Table VIA 5N represents the traditional oxidative hair dye technique with the coupler resorcinol. As mentioned in the Background, traditional resorcinol oxidative dyes produce a rich well developed color spectrum and have rapid color development with a resorcinol control of L* negative progression. The comparison of 5N-1 and 5N-2 of Tables VIC and VIA respectively demonstrates this resorcinol control of oxidative dye compositions containing resorcinol. They darken through about 20 minutes to 25 minutes and then significantly to essentially reach a steady state for the darkening effect whereas without resorcinol, they darken continuously past 30 minutes and more.

Table VIB, the composition 5N-3 (glycine and resorcinol) negates the resorcinol action control of resorcinol shown by Table VIA, 5N-2. Table VIB with composition 5N-3 follows the composition portfolio described by March in U.S. Pat. No. 7,481,846, discussed in the Background. Marsh adds the glycine to her resorcinol compositions to protect hair strands from oxidative damage. One would expect that formulas using Marsh's addition would behave like resorcinol formulations in that they would continue to show a resorcinol control of the L* negative progression or would enhance this effect since March indicates that resorcinol and glycine have the same scavenger property. However, the experimental results for 5N-3 show an adverse effect upon the L* negative progression produced by 5N-2. Composition 5N-3 exhibits a slowing of the L*color progression and its continuation long past the time period for establishing steady state produced by 5N-2. This indicates that glycine negates the resorcinol control of L* negative progression and that glycine has no affirmative effect for resorcinol control.

What is the result of L* progression of oxidative dye compositions from which resorcinol has been removed?

Table V showing the color results for Shades 2N-1, 3N-1, 4N-1 and 5N-1 present such resorcinol free oxidative dye composition results and do not contain glycine. The experimental results for the Shades 2N-1 through 5N-1 of Table V show that its color development progresses along the L* axis past 30 minutes.

These results demonstrate that without resorcinol, the primary precursor/coupler formulation with secondary precursors and couplers suffers from the problem of continued darkening. This continued darkening presents a significant challenge to hair care professionals. Application of a non-resorcinol oxidative hair dye formulation to a first portion of hair will continue to darken until a second portion of hair is treated and the entire head of hair rinsed. The result is portions of hair with differing darkened colors.

In contrast to the expectation of no L* control as shown by Table V 2N-1 through 5N-1 (TC-1 compositions without resorcinol, without glycine), Table V 2N-4, 3N-4, 4N-4 and 5N-4 (TC-4 with glycine) shows the pseudo-resorcinol action control of negative L* progression mimicking those of the resorcinol test compositions TC-2 of Table V 2N-2, 3N-2, 4N-2 and 5N-2.

These examples demonstrate the surprising pseudo-resorcinol control exhibited by addition of an amino acid to a non-resorcinol hair coloring composition of at least the primary precursor and coupler MBB and Aminol. The experiments also demonstrate that use of an amino acid in a resorcinol hair dye composition (Table V, 2N3-5N3) such as that described by Marsh in U.S. Pat. No. 7,481,846 adversely affects the control of L* negative progression produced by resorcinol.

Pseudo-Resorcinol Action Control of Invention Embodiment Versus the L* Progression of a Commercial Oxidative Dye with No Resorcinol The pseudo-resorcinol control of use of an embodiment of the oxidative hair coloring composition according to the invention and use of a commercial hair color system with no resorcinol were examined. The pseudo-resorcinol control results for the embodiment of the present invention show no significant negative progression along the L* axis after about 10-20 minutes where the L* development is examined for at least 25 minutes while the L* results for the commercial non-resorcinol system continue to progress in the L* negative direction past 25 minutes.

Pursuant to the hair swatch, color treatment procedure described above, hair swatches are prepared with the oxidative hair coloring composition and the comparative commercial hair color composition (See composition notes with Tables VIIA and VIIB). The colors of the resulting hair swatches are examined by the Minolta procedure given above to determine the L*a*b* color space provided by the oxidative hair coloring composition and the comparative non-resorcinol composition.

Tables VIIA and VIIB present the results of this comparative experiment. Tables VIIA (comparative) and VIIB (invention embodiment) demonstrate that the L* axis color development of the embodiment of the oxidative hair coloring composition according to the invention does not progress in the negative direction along the L* axis of the CIELAB color space after about 20 to 25 minutes while the L* axis color development of the commercial non-resorcinol hair color composition continues to develop in the negative direction along the L* axis of the CIELAB color space past 25 minutes. These results show the initial rapid color development and the succeeding steady state status of color development according to the invention as described above in the above-described Pseudo-Resorcinol Control section, pages 12-14.

TABLE VIIA[1]

| Data Name | L*(D65) | a*(D65) | b*(D65) |
|---|---|---|---|
| Commercial Black 10 min | 20.35 | 2.53 | 3.35 |
| Commercial Black 15 min | 18.72 | 2.17 | 2.38 |
| Commercial Black 20 min | 17.83 | 1.88 | 1.81 |
| Commercial Black 25 min | 17.33 | 1.46 | 1.62 |

1) Commercial Non-Resorcinol Hair Color Composition Ingredients

Tint composition: water, alcohol, PEG-4-rapeseed amide, glyceryl lauryl ether, deceth-3, propylene glycol, laureth-5 carboxylic acid, ammonium hydroxide, dipropylene glycol, hexylene glycol, poloxamer 338, ammonium bicarbonate oleyl alcohol, ethanol amine, perfume, ammonium thiolactate, EDTA, erythorbic acid, thioglycerin, sodium metabisulfite, toluene 2,5-diamine, hydroxybenzomorpholine, m-aminophenol, N,N-(bis(2-hydroxyethyl)-p-phenylene diamine sulfate, 6-hydroxyindole, p-aminophenol, 2,4-diaminophenoxyethanol hydrochloride.

Oxidizer composition: hydrogen peroxide, water, cetearyl alcohol, sodium stannate, trideceth-2 carboxamide mea, pentasodium pentetete, Phosphoric acid, ceteareth-25, tetrasodium pyrophosphate, glycerin.

TABLE VIIB[2]

| Data Name | L*(D65) | a*(D65) | b*(D65) |
|---|---|---|---|
| Emb black shade-10 min | 21.34 | 1.13 | 4.38 |
| Emb black shade-15 min | 19.83 | 1.23 | 3.66 |
| Emb black shade-20 min | 18.75 | 1.33 | 4.5 |
| Emb black shade-25 min | 19.17 | 1.35 | 4.62 |

2) Embodiment (Emb) Black Shade Oxidative Hair Coloring Composition Ingredients

Tint composition: water, cetearyl alcohol, dicetyl phosphate and ceteth-10 phosphate, steareth-200, propylene glycol, xanthan gum, glycine, trisodium ethylenediamine disuccinate, sodium hydroxide, ascorbic acid, disodium EDTA, sodium sulfite, 2-methoxymethyl-p-phenylene diamine, p-aminophenol, 2,4-diaminophenoxyethanol, hydroxy ethyl-3,4-methylenedioxy aniline, 4-amino-2-hydroxytoluene, m-aminophenol, ammonium carbonate, sheer amethyst.

Oxidizer composition: water, hydrogen peroxide, cetearyl alcohol, sodium cetearyl sulfate, paraffinum, salicylic acid, buffer of disodium phosphate/phosphoric acid and etidronic acid.

These results (Tables VIIA, VIIB) demonstrate the pseudo-resorcinol control of the oxidative hair coloring composition according to the invention relative to the continued L-darkening property of a comparative resorcinol free commercial composition.

Statement of Embodiments

The Statements of the Invention set forth further Embodiments of the Invention and provide details described above as well as additional details according to the Invention. The Statements supplement and expand the description of embodiments of the oxidative hair coloring composition and the corresponding method set forth in the Detailed Description. These Statements provide further disclosure of these aspects, features and parameters and may serve as claims of the invention. Discrepancies between the Statements and Detailed Description are to be considered to be additive rather than subtractive.

Statement 1A.

1A. A method for coloring hair comprising applying to hair an oxidative hair coloring composition comprising a cosmetically acceptable medium and at least components A, B and C wherein:

A) is a precursor comprising 2-methoxymethyl-p-phenylene diamine (MBB) of Formula I, its addition salts, its solvates and/or solvates of its salts;

Formula I

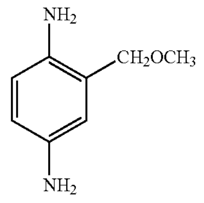

B) is a coupler comprising hydroxyethyl-3,4-methylenedioxyaniline (Aminol) of Formula II, its addition salts, its solvates and/or solvates of its salts, Formula II

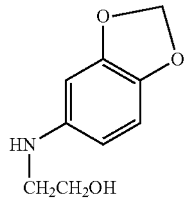

C) an L* mixture of a source of carbonate and/or bicarbonate source, a source of ammonium cation and an amino acid selected from glycine, alanine, arginine, proline, serine, threonine, lysine or any combination thereof;

the oxidative hair coloring composition is free of resorcinol and C1-C10 alkyl resorcinol and halo resorcinol; and the oxidative hair coloring composition displays pseudo-resorcinol control of the progression of color in the negative direction along the L* axis of the CIELAB color space.

Statement 1B.

1B. A method for coloring hair comprising applying to hair an oxidative hair coloring composition comprising a cosmetically acceptable medium and at least components A, B and C wherein:

A) is a precursor comprising i) 2-methoxymethyl-p-phenylene diamine (MBB) of Formula I, its addition salts, its solvates and/or solvates of its salts;

Formula I

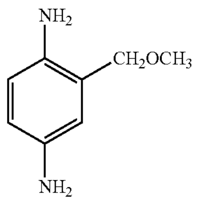

and ii. optional secondary precursor p-aminophenol (PAP), its addition salts, its solvates and/or solvates of its salts at; and, B) is a coupler comprising i) hydroxyethyl-3,4-methylenedioxyaniline (Aminol) of Formula II, its addition salts, its solvates and/or solvates of its salts, Formula II

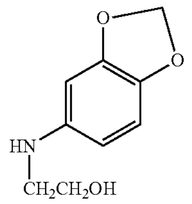

and one or more secondary couplers comprising:

ii) 2,4-diaminophenoxyethanol (DPE), its addition salts, its solvates and/or solvates of its salts;

iii) m-aminophenol (MAP), its addition salts, its solvates and/or solvates of its salts; and iv) 4-amino-2-hydroxy toluene (AHT), its addition salts, its solvates and/or solvates of its salts; and, v) ethyl ortho-amino phenol (EOAP) its addition salts, its solvates and/or solvates of its salts;

C) an L* mixture of a source of carbonate and/or bicarbonate, a source of ammonium cation and an amino acid selected from glycine, alanine, arginine, proline, serine, threonine, lysine or any combination thereof;

the oxidative hair coloring composition is free of resorcinol and C1-C10 alkyl resorcinol and halo resorcinol; and the oxidative hair coloring composition displays pseudo-resorcinol control of color progression in the negative direction along the L* axis of the CIELAB color space.

Statement 1C.

1C. A method for coloring hair comprising applying to hair an oxidative hair coloring composition comprising a cosmetically acceptable, basic pH medium with at least hydrogen peroxide; a source of carbonate and/or bicarbonate; a cation for the source of carbonate and/or bicarbonate selected from an alkali metal cation, an alkaline earth metal cation or an organic or inorganic ammonium cation selected from ammonium hydroxide, protonated trialkyl ammonium halide, tetraalkyl ammonium halide or hydroxide, aminoalkyl alcohol; and an amino acid selected from glycine, alanine, arginine, proline, serine, threonine, lysine or any combination thereof and at least components A and B wherein:

A) is a precursor comprising i. 2-methoxymethyl-p-phenylene diamine (MBB) of Formula I, its addition salts, its solvates and/or solvates of its salts;

Formula II

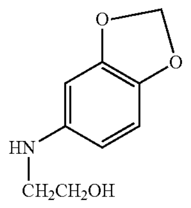

and ii. optional secondary precursor p-aminophenol (PAP), its addition salts, its solvates and/or solvates of its salts at; and, B) is a coupler comprising i) hydroxyethyl-3,4-methylenedioxyaniline (Aminol) of Formula II, its addition salts, its solvates and/or solvates of its salts, at Formula II

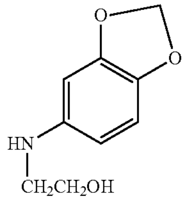

and one or more optional secondary couplers comprising:

ii) 2,4-diaminophenoxyethanol (DPE), its addition salts, its solvates and/or solvates of its salts;

iii) m-aminophenol (MAP), its addition salts, its solvates and/or solvates of its salts; and iv) 4-amino-2-hydroxy toluene (AHT), its addition salts, its solvates and/or solvates of its salts; and, v) ethyl ortho-amino phenol (EOAP), its addition salts, its solvates and/or solvates of its salts;

the oxidative hair coloring composition is free of resorcinol and C1-C10 alkyl resorcinol and halo resorcinol; and, the oxidative hair coloring composition displays pseudo-resorcinol control of color progression in the negative direction along the L* axis of the CIELAB color space.

Statement 1D.

1D. A method for coloring hair comprising applying to hair an oxidative hair coloring composition comprising a cosmetically acceptable medium and at least components A, B and C wherein:

A) is a precursor comprising i. 2-methoxymethyl-p-phenylene diamine (MBB) of Formula I, its addition salts, its solvates and/or solvates of its salts;

Formula I

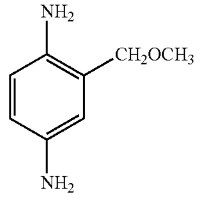

and ii. optional secondary precursor comprising p-aminophenol (PAP), its addition salts, its solvates and/or solvates of its salts; and, B) is a coupler mixture comprising i) hydroxyethyl-3,4-methylenedioxyaniline (Aminol) of Formula II, Formula II

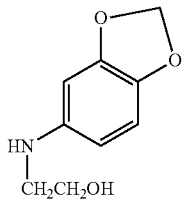

its addition salts, it solvates and/or solvates of its salts, and secondary couplers comprising:

ii) 2,4-diaminophenoxyethanol (DPE), its addition salts, its solvates and/or solvates of its salts;

iii) m-aminophenol (MAP), its addition salts, its solvates and/or solvates of its salts;

iv) 4-amino-2-hydroxy toluene (AHT), its addition salts, its solvates and/or solvates of its salts; and, v) optional ethyl ortho-amino phenol (EOAP), its addition salts, its solvates and/or solvates of its salts;

C) an L* mixture of a source of carbonate and/or bicarbonate, a source of ammonium cation and an amino acid selected from glycine, alanine, arginine, proline, serine, threonine, lysine or any combination thereof;

the oxidative hair coloring composition is free of resorcinol and C1-C10 alkyl resorcinol and halo resorcinol; and, the oxidative hair coloring composition displays pseudo-resorcinol control of color progression in the negative direction along the L* axis of the CIELAB color space.

Statement 2. The method for coloring hair according to any of statements 1A, 1B, 1C and 1D wherein the concentrations of MBB, AMINOL, as well as the concentrations of the secondary precursor and couplers PAP, DPE, MAP AHT AND EOAP when included are:

a) MBB at a concentration of about 0.1 wt % to about 10 wt %;

b) AMINOL at a concentration of from about 0.1 wt % to about 5 wt % c) PAP at a concentration of about 0.1 wt % to about 3 wt %;

d) DPE at a concentration of about 0.1 wt % to about 3 wt %;

e) MAP at a concentration of about 0.1 wt % to about 3 wt %;

f) AHT at a concentration of about 0.05 wt % to about 1.5 wt %; and g) EOAP at a concentration of about 0.01 wt % to about 2 wt %.

Statement 3. The method for coloring hair according to any of statements 1A, 1B, 1C and 1D wherein the concentrations of MBB, AMINOL, as well as the concentrations of secondary precursor and couplers PAP, DPE, MAP AHT AND EOAP when included are:

a) MBB at a concentration of about 0.5 wt % to about 6 wt %;

b) AMINOL at a concentration of from about 0.5 wt % to about 4 wt % c) PAP at a concentration of about 0.2 wt % to about 1.5 wt %;

d) DPE at a concentration of about 0.1 wt % to about 2.5 wt %;

e) MAP at a concentration of about 0.1 wt % to about 2 wt %;

f) AHT at a concentration of about 0.05 wt % to about 1 wt %; and g) EOAP at a concentration of about 0.01 wt % to about 1.5 wt %.

Statement 4. The method for coloring hair according to any of the preceding statements further comprising one or more of an additional subsidiary coupler and/or one or more of an additional subsidiary precursor or any combination thereof wherein:

the at least one additional subsidiary coupler comprises 6-hydroxybenzomorpholine, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 2-amino-5-ethylphenol, 6-amino-o-cresol, 2-amino-4-hydroxyethylaminoanisole, 1,3-bis-(2,4-diaminophenoxy) propane, 2,6-dihydroxyethylaminotoluene, 1-naphthol, 2-methyl-1-naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindoline, phenyl methyl pyrazolone, hydroquinone, 4-formyl-1-methylquinolinium-p-toluenesulfonate, 2-amino-6-chloro-4-nitrophenol, 3,4-methylenedioxyphenol and addition salts, solvates and/or solvates of salts thereof, and any combination thereof;

the at least one additional subsidiary precursor comprises at least one of hydroxyethyl-p-phenylenediamine sulphate, hydroxypropyl bis(n-hydroxyethyl-p-phenylenediamine), 2-chloro-p-phenylenediamine, p-methylaminophenol, 4-amino-m-cresol, 6-amino-m-cresol, bis(5-amino-2-hydroxyphenyl) methane, tetraaminopyrimidine, 2,5,6-triamino-4-pyrimidinol, 4,5-diamino-1-(2-hydroxyethyl)pyrazol, 2,3-diaminodihydroxypyrazolopyrazolone dimethosulfonate, 4,5-diamino-1-hexylpyrazol, 2,3-diamino-6,7-dihydro-1H,5H-pyrazolo[1,2-a]pyrazol-1-one, hydroxypropyl-p-phenylenediamine, dimethylpiperazinium aminopyrazolopyridine chloride hydrochloride, 4,5-diamino-3-methyl-1H-pyrazole-1-ethanol, 1-hexyl-3-methyl-1H-pyrazole-4,5-diamine, methylimidazoliumpropyl p-phenylenediamine, hydroxyethoxy aminopyrazolopyridine, 2-(2,5-diaminophenyl)ethanol, N,N-bis-(2-hydroxyethyl)-p-phenylenediamine and addition salts, solvates and/or solvates of salts thereof, and any combination thereof.

Statement 5. The method for coloring hair according to any of the preceding statements 1A, 1B, 1D, 2-4 further comprising a pH basic medium and hydrogen peroxide present in an amount in a range of from about 1.0 wt % to about 12.0 wt % relative to the total weight of the oxidative hair coloring composition.

Statement 6. The method for coloring hair according to preceding statement 1C wherein the hydrogen peroxide is present in an amount in a range of from about 1.0 wt % to about 12.0 wt % relative to the total weight of the oxidative hair coloring composition.

Statement 7. The method for coloring hair according to preceding statements further comprising an alkalizing agent comprising alkali metal hydroxide and/or ammonium hydroxide wherein each of the alkalizing agent and the source of carbonate/bicarbonate is present in an amount in a range of from about 0.1 wt % to about 10.0 wt % and the selected amino acid or a combination thereof is present in an amount of from about 0.01 wt % to about 15.0 wt %, preferably 0.1 wt % to about 10.0 wt %, more preferably from about 1 wt % to about 6 wt % and wherein the wt %'s are relative to the total weight of the oxidative hair coloring composition.

Statement 8. The method for coloring hair according to any of the preceding statements, further comprising at least a chassis comprising at least a mixture of a three-component phosphate surfactant comprising cetearyl alcohol, dicetyl phosphate and ceteth-10 phosphate, a nonionic surfactant comprising steareth-200, xanthan gum, a chelator comprising one or more of EDDS, MGDA, GLDA and DTPHP, a solvent-humectant comprising glycol and a solvent of water.

Statement 9. The method for coloring hair according to any of the preceding statements further comprising one or more anionic and/or nonionic surfactants comprising at least one of a phosphate anionic surfactant, a nonionic polyethoxy alkyl ether surfactant, a fatty alcohol or any combination thereof, wherein each is present in an amount of from about 0.1 wt % to about 15 wt % relative to the total weight of the hair coloring composition.

Statement 10. The method for coloring hair according to any of the preceding statements further comprising one or more of components J, K and L wherein:

component J comprises dicetyl phosphate, ceteth-10 phosphate and steareth-2 to 200;

component K comprises one or more of a C8-C20 fatty alcohol;

component L comprises at least one of ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), methylglycinediacetic acid (MGDA), tetrasodium glutamate diacetate (GLDA), salts, derivatives, and/or any combination thereof.

Statement 11. The method for coloring hair according to any of the preceding statements, further comprising one or more ingredients selected from a thickener, a conditioner, an anionic and/or nonionic surfactant, humectant/emulsifier, an antioxidant, a pH control agent, a sunscreen, opacifying agent, sodium sulfate, xanthan gum, ethoxydiglycol, oleamide MIPA, beeswax, hydrolyzed keratin, polyquaternium-22, soytrimonium chloride, dicetydimonium chloride, glycerin, propylene glycol, lanolin alcohol, hexylene glycol, dipropylene glycol, ethanol, isopropanol, citric acid, sodium hydroxide, etidronic acid, ascorbic acid, sodium sulfite, vitamin E, fragrance and/or any combination thereof.

Statement 12. The method for coloring hair according to any of the preceding statements wherein the pseudo-resorcinol control mimics the resorcinol control of L* negative color progression of the oxidative hair coloring composition wherein resorcinol is substituted for the amino acid.

Statement 13. The method for coloring hair according to statement 12 wherein the pseudo-resorcinol control manages the L* color progression so as to reach substantially a constant level over a period of from about 20 to about 30 minutes.

Statement 14. A tint composition comprising a cosmetically acceptable medium of a basic pH and at least components A, B and C wherein:

A) is a precursor comprising 2-methoxymethyl-p-phenylene diamine (MBB) of Formula I, its addition salts, its solvates and/or solvates of its salts;

Formula I

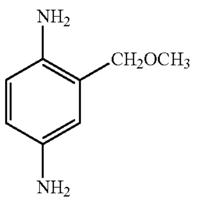

B) is a coupler comprising hydroxyethyl-3,4-methylenedioxyaniline (Aminol) of Formula II, its addition salts, its solvates and/or solvates of its salts, Formula II

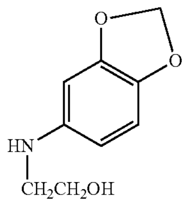

C) is an L* mixture of a source of carbonate and/or bicarbonate, a source of ammonium cation and an amino acid selected from glycine, alanine, arginine, proline, serine, threonine, lysine or any combination thereof, an optional alkalizer comprising alkali metal hydroxide and/or ammonium hydroxide and the tint composition is free of resorcinol, C1-C10 alkyl resorcinol and halo resorcinol.

Statement 15. The tint composition according to statement 14 further comprising a separate acidic, buffered oxidizer composition of at least hydrogen peroxide.

Statement 16. An oxidative hair coloring composition comprising a cosmetically acceptable medium and at least components A, B and C wherein:

A) is a precursor comprising 2-methoxymethyl-p-phenylene diamine (MBB) of Formula I, its addition salts, its solvates and/or solvates of its salts;

Formula I

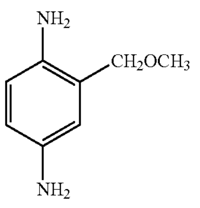

B) is a coupler comprising hydroxyethyl-3,4-methylenedioxyaniline (Aminol) of Formula II, its addition salts, its solvates and/or solvates of its salts, Formula II

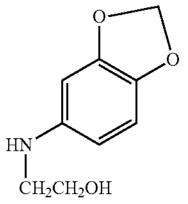

C) is an L* mixture of a source of carbonate and/or bicarbonate source, a source of ammonium cation and an amino acid selected from glycine, alanine, arginine, proline, serine, threonine, lysine or any combination thereof;

the oxidative hair coloring composition is free of resorcinol and C1-C10 alkyl resorcinol and halo resorcinol; and the oxidative hair coloring composition has a property of pseudo-resorcinol control of the progression of color in the negative direction along the L* axis of the CIELAB color space.

Statement 17. An oxidative hair coloring composition comprising a cosmetically acceptable medium and at least components A, B and C wherein:

A) is a precursor comprising i) 2-methoxymethyl-p-phenylene diamine (MBB) of Formula I, its addition salts, its solvates and/or solvates of its salts;

Formula I

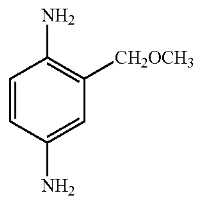

and ii. optional secondary precursor p-aminophenol (PAP), its addition salts, its solvates and/or solvates of its salts at; and, B) is a coupler comprising i) hydroxyethyl-3,4-methylenedioxyaniline (Aminol) of Formula II, its addition salts, its solvates and/or solvates of its salts, Formula II

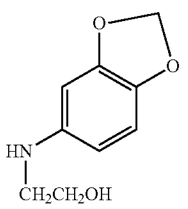

and one or more optional secondary couplers comprising:

ii) 2,4-diaminophenoxyethanol (DPE), its addition salts, its solvates and/or solvates of its salts;

iii) m-aminophenol (MAP), its addition salts, its solvates and/or solvates of its salts;

iv) 4-amino-2-hydroxy toluene (AHT), its addition salts, its solvates and/or solvates of its salts; and, v) ethyl ortho-amino phenol (EOAP), its addition salts, its solvates and/or solvates of its salts;

C) is an L* mixture of a source of carbonate and/or bicarbonate, a source of ammonium cation and an amino acid selected from glycine, alanine, arginine, proline, serine, threonine, lysine or any combination thereof;

the oxidative hair coloring composition is free of resorcinol and C1-C10 alkyl resorcinol and halo resorcinol; and the oxidative hair coloring composition has a property of pseudo-resorcinol control of color progression in the negative direction along the L* axis of the CIELAB color space.

Statement 18. An oxidative hair coloring composition according to statement 16 or 17 further comprising a buffered pH basic medium, hydrogen peroxide present in an amount in a range of from about 1.0 wt % to about 12.0 wt %, an alkalizing agent comprising alkali metal hydroxide and/or ammonium hydroxide wherein each of the alkalizing agent and the source of carbonate/bicarbonate is present in an amount in a range of from about 0.1 wt % to about 10.0 wt % and the selected amino acid or a combination thereof is present in an amount of from about 0.01 wt % to about 15.0 wt %, preferably 0.1 wt % to about 10.0 wt %, more preferably from about 1 wt % to about 6 wt % and wherein the wt %'s are relative to the total weight of the oxidative hair coloring composition.

Statement 19. An oxidative hair coloring composition comprising a cosmetically acceptable, basic pH medium with at least hydrogen peroxide; a source of carbonate and/or bicarbonate; a cation for the source of carbonate and/or bicarbonate selected from an alkali metal cation, an alkaline earth metal cation or an organic or inorganic ammonium cation selected from ammonium hydroxide, protonated trialkyl ammonium halide, tetraalkyl ammonium halide or hydroxide, aminoalkyl alcohol; and an amino acid selected from glycine, alanine, arginine, proline, serine, threonine, lysine or any combination thereof and at least components A and B wherein:

A) is a precursor comprising i. 2-methoxymethyl-p-phenylene diamine (MBB) of Formula I, its addition salts, its solvates and/or solvates of its salts;

Formula I

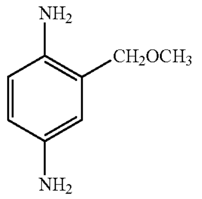

and ii. optional secondary precursor p-aminophenol (PAP), its addition salts, its solvates and/or solvates of its salts at; and, B) is a coupler comprising i) hydroxyethyl-3,4-methylenedioxyaniline (Aminol) of Formula II, its addition salts, it solvates and/or solvates of its salts, at Formula II

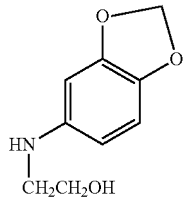

and one or more optional secondary couplers comprising:

ii) 2,4-diaminophenoxyethanol (DPE), its addition salts, its solvates and/or solvates of its salts;

iii) m-aminophenol (MAP), its addition salts, its solvates and/or solvates of its salts; and iv) 4-amino-2-hydroxy toluene (AHT), its addition salts, its solvates and/or solvates of its salts; and, v) ethyl ortho-amino phenol (EOAP), its addition salts, its solvates and/or solvates of its salts;

the oxidative hair coloring composition is free of resorcinol and C1-C10 alkyl resorcinol and halo resorcinol; and, the oxidative hair coloring composition has a property of pseudo-resorcinol control of color progression in the negative direction along the L* axis of the CIELAB color space.

Statement 20. A kit comprising:

A. a tint composition comprising a cosmetically acceptable medium, an alkalizer, an L* mixture of a source of carbonate/bicarbonate, a source of ammonium cation and an amino acid selected from glycine, alanine, arginine, proline, serine, threonine, lysine or any combination thereof, and a precursor of at least MBB and a coupler of at least Aminol; and, B. an oxidizer composition comprising at least a cosmetically acceptable medium, hydrogen peroxide, a fatty alcohol, an anionic surfactant and a buffered acid to maintain an acidic pH of the oxidizer composition;

wherein the tint composition component and the oxidizer composition component are maintained separately and are free of resorcinol and C1-C10 alkyl resorcinol and halo resorcinol.

Statement 21. A kit according to statement 20 wherein the tint composition component further comprises:

i) dicetyl phosphate, ceteth-10 phosphate and steareth-2 to 200;

ii) one or more of a C8-C20 fatty alcohol;

at least one chelator selected from ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), methylglycinediacetic acid (MGDA), tetrasodium glutamate diacetate (GLDA), salts, derivatives, and/or any combination thereof, and iii) optionally one or more ingredients selected from a thickener, a conditioner, a humectant/emulsifier, an antioxidant, a pH control agent, a sunscreen, opacifying agent, sodium sulfate, xanthan gum, ethoxydiglycol, oleamide MIPA, beeswax, hydrolyzed keratin, polyquaternium-22, soytrimonium chloride, dicetydimonium chloride, glycerin, propylene glycol, lanolin alcohol, hexylene glycol, dipropylene glycol, ethanol, isopropanol, citric acid, sodium hydroxide, etidronic acid, ascorbic acid, sodium sulfite, vitamin E, fragrance and/or any combination thereof.

Statement 22. The kit according to statement 20 or 21 wherein the combination of the tint composition and the oxidizer composition has a property of pseudo-resorcinol control of color progression in the negative direction along the L* axis of the CIELAB color space.

Statement 23. A method for coloring hair with the oxidative hair coloring composition formed from the kit according to statement 20, 21 or 22 comprising the steps of:

a. combining the tint composition cand the oxidizer composition of the kit to provide the oxidative hair coloring composition;
b. applying the oxidative hair coloring composition of step a to the hair,
c. allowing the oxidative hair coloring composition to remain on the hair for a period of at least 20 to 30 minutes, and
d. subsequently rinsing the composition from the hair.

Statement 24. The method for coloring hair according to statement 23 wherein the oxidative hair coloring composition displays pseudo-resorcinol control of the color progression in the negative direction along the L* axis of the CIELAB color space.

Statement 25. The method for coloring hair according to statement 24 wherein the pseudo-resorcinol control manages the color progression and reaches substantially a steady state in a period of about 20 to 30 minutes.

Statement 26. Use of the oxidative hair coloring oxidative hair coloration composition recited by any of preceding statements 16-19 for oxidative coloration of hair.

Miscellaneous Statements

The invention has been described broadly and generically herein. Each of the narrower species and subgeneric groupings falling within the generic disclosure also form part of the invention. This includes the generic description of the invention with a proviso or negative limitation removing any matter from the genus, regardless of whether or not the excised material is specifically recited herein. The inventions, examples, results and statement of embodiments described, stated and claimed herein may have attributes and embodiments include, but not limited to, those set forth or described or referenced in this application.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed and as provided by the statements of embodiments. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims and the statements of embodiments.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, textbook or other referenced material or document.

The written description of this patent application includes all claims, examples and statements of embodiments. All claims and statements of embodiments including all original claims are hereby incorporated by reference in their entirety into the written description portion of the specification and the right is reserved to physically incorporate into the written description or any other portion of the application any and all such claims and statements of embodiments. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims and the statements of embodiments. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims and the statements of embodiments.

The specific methods and compositions described herein are representative of preferred nonlimiting embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", "providing" and the like are to be read expansively and without limitation.

The methods and processes illustratively described herein suitably may be practiced in differing orders of steps, and that they are not necessarily restricted to the orders of steps indicated herein or in the claims.

What is claimed is:

1. A method for coloring hair comprising applying to hair an oxidative hair coloring composition comprising a cosmetically acceptable medium of a basic pH and at least components A, B and C wherein:

A) is a precursor comprising 2-methoxymethyl-p-phenylene diamine (MBB) of Formula I, its addition salts, its solvates and/or solvates of its salts;

Formula I

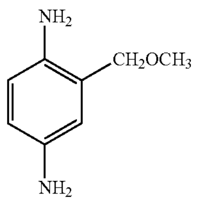

B) is a coupler comprising hydroxyethyl-3,4-methylenedioxyaniline (Aminol) of Formula II, its addition salts, its solvates and/or solvates of its salts, Formula II

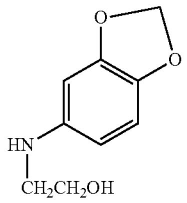

C) is an L* mixture of a source of carbonate and/or bicarbonate, a source of ammonium cation and an amino acid selected from glycine;

the composition is free of resorcinol, C1-C10 alkyl resorcinol and halo resorcinol;

the composition displays pseudo-resorcinol action control of the color progression in the negative direction along the L* axis of the CIELAB color space; and the composition comprises hydrogen peroxide, and an optional alkalizer of an alkali metal hydroxide and/or ammonium hydroxide.

2. The method for coloring hair wherein the oxidative hair coloring composition of claim 1 further comprises:

one or more of a secondary precursor and a secondary coupler wherein the secondary precursor comprises at least p-aminophenol (PAP), its addition salts, its solvates and/or solvates of its salts;

and the secondary coupler comprises at least one or more of 2,4-diaminophenoxyethanol (DPE), its addition salts, its solvates and/or solvates of its salts, m-aminophenol (MAP), its addition salts, its solvates and/or solvates of its salts, 4-amino-2-hydroxy toluene (AHT), its addition salts, its solvates and/or solvates of its salts; and, ethyl ortho-amino phenol (EOAP) its addition salts, its solvates and/or solvates of its salts.

3. The method for coloring hair according to claim 1 wherein the concentrations of MBB and AMINOL, comprise:

a) MBB at a concentration of about 0.1 wt % to about 10 wt %;

b) AMINOL at a concentration of from about 0.1 wt % to about 5 wt %.

4. The method for coloring hair according to claim 2 wherein the concentrations of PAP, DPE, MAP AHT and EOAP comprise:

a. PAP at a concentration of about 0.1 wt % to about 3 wt %;

b. DPE at a concentration of about 0.1 wt % to about 3 wt %;

c. MAP at a concentration of about 0.1 wt % to about 3 wt %;

d. AHT at a concentration of about 0.05 wt % to about 1.5 wt %; and e. EOAP at a concentration of about 0.01 wt % to about 2 wt %.

5. The method for coloring hair according to claim 1 further comprising one or more of an additional subsidiary coupler or any combination thereof, and/or one or more of an additional subsidiary precursor or any combination thereof wherein:

the at least one additional subsidiary coupler comprises 6-hydroxybenzomorpholine, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 2-amino-5-ethylphenol, 6-amino-o-cresol, 2-amino-4-hydroxyethylaminoanisole, 1,3-bis-(2,4-diaminophenoxy)propane, 2,6-dihydroxyethylaminotoluene, 1-naphthol, 2-methyl-1-naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindoline, phenyl methyl pyrazolone, hydroquinone, 4-formyl-1-methylquinolinium-p-toluenesulfonate, 2-amino-6-chloro-4-nitrophenol, 3,4-methylenedioxyphenol and addition salts, solvates and/or solvates of salts thereof, and any combination thereof, the at least one additional subsidiary precursor comprises at least one of hydroxyethyl-p-phenylenediamine sulphate, hydroxypropyl bis(n-hydroxyethyl-p-phenylenediamine), 2-chloro-p-phenylenediamine, p-methylaminophenol, 4-amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol, 2,3-diamino-dihydroxypyrazolopyrazolone dimethosulfonate, 4,5-diamino-1-hexylpyrazol, 2,3-diamino-6,7-dihydro-1H, 5H-pyrazolo[1,2-a]pyrazol-1-one, hydroxypropyl-p-phenylenediamine, dimethylpiperazinium aminopyrazolopyridine chloride hydrochloride, 4,5-diamino-3-methyl-1H-pyrazole-1-ethanol, 1-hexyl-3-methyl-1H-pyrazole-4,5-diamine, methylimidazoliumpropyl p-phenylenediamine, hydroxyethoxy aminopyrazolopyridine, 2-(2,5-diaminophenyl)ethanol, N,N-bis-(2-hydroxyethyl)-p-phenylenediamine and addition salts, solvates and/or solvates of salts thereof, and any combination thereof.

6. The method for coloring hair according to claim 1 wherein each of the alkalizing agent and the source of carbonate/bicarbonate is present in a range of from about 0.1 wt % to about 10.0 wt % and the selected amino acid is present in an amount of from about 0.01 wt % to about 15.0 wt %, and the hydrogen peroxide is present in a range of from about 1.0 wt % to about 12.0 wt % wherein the wt %'s are relative to the total weight of the oxidative hair coloring composition.

7. The method for coloring hair according to claim 1 wherein the oxidative hair coloring composition further comprises one or more of components J, K and L wherein:

component J comprises dicetyl phosphate, ceteth-10 phosphate and steareth-2 to 200;

component K comprises one or more of a C8-C20 fatty alcohol;

component L comprises at least one of ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), methylglycinediacetic acid (MGDA), tetrasodium glutamate diacetate (GLDA), salts, derivatives, and/or any combination thereof.

8. A method for coloring hair using a tint composition to form an oxidative hair coloring composition wherein the tint composition comprises cosmetically acceptable medium of a basic pH and at least components A, B and C wherein:

A) is a precursor comprising 2-methoxymethyl-p-phenylene diamine (MBB) of Formula I, its addition salts, its solvates and/or solvates of its salts;

Formula I

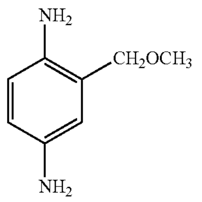

B) is a coupler comprising hydroxyethyl-3,4-methylenedioxyaniline (Aminol) of Formula II, its addition salts, its solvates and/or solvates of its salts, Formula II

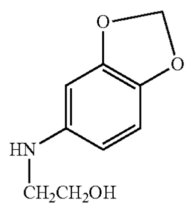

C) is an L* mixture of a source of carbonate and/or bicarbonate, a source of ammonium cation and an amino acid selected from glycine;

the tint composition is free of resorcinol, C1-C10 alkyl resorcinol and halo resorcinol; and the tint composition comprises an optional alkalizing agent of alkali metal hydroxide and/or ammonium hydroxide.

9. The method for coloring hair according to claim 8 wherein the tint composition further comprises: one or more of a secondary precursor and a secondary coupler wherein the secondary precursor comprises at least p-aminophenol (PAP), its addition salts, its solvates and/or solvates of its salts; and the secondary coupler comprises at least one or more of 2,4-diaminophenoxyethanol (DPE), its addition salts, its solvates and/or solvates of its salts, m-aminophenol (MAP), its addition salts, its solvates and/or solvates of its salts, 4-amino-2-hydroxy toluene (AHT), its addition salts, its solvates and/or solvates of its salts; and ethyl ortho-amino phenol (EOAP), its addition salts, its solvates and/or solvates of its salts.

10. The method of coloring hair according to claim 8 wherein tint composition further comprises one or more of an additional subsidiary coupler and/or one or more of an additional subsidiary precursor or any combination thereof wherein:

the at least one additional subsidiary coupler comprises 6-hydroxybenzomorpholine, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 2-amino-5-ethylphenol, 6-amino-o-cresol, 2-amino-4-hydroxyethylaminoanisole, 1,3-bis-(2,4-diaminophenoxy)propane, 2,6-dihydroxyethylaminotoluene, 1-naphthol, 2-methyl-1-naphthol, 1,5-naphthalenediol, 2,7-naphthalenediol, 1-acetoxy-2-methylnaphthalene, 2,6-dihydroxy-3,4-dimethylpyridine, 2,6-dimethoxy-3,5-pyridinediamine, 3-amino-6-methoxy-2-(methylamino)-pyridine, 2-amino-3-hydroxypyridine, 2,6-diaminopyridine, dihydroxyindoline, phenyl methyl pyrazolone, hydroquinone, 4-formyl-1-methylquinolinium-p-toluenesulfonate, 2-amino-6-chloro-4-nitrophenol, 3,4-methylenedioxyphenol and addition salts, solvates and/or solvates of salts thereof, and any combination thereof;

the at least one additional subsidiary precursor comprises at least one of hydroxyethyl-p-phenylenediamine sulphate, hydroxypropyl bis(n-hydroxyethyl-p-phenylenediamine), 2-chloro-p-phenylenediamine, p-methylaminophenol, 4-amino-m-cresol, 6-amino-m-cresol, bis(5-amino-2-hydroxyphenyl)methane, tetraaminopyrimidine, 2,5,6-triamino-4-pyrimidinol, 4,5-diamino-1-(2-hydroxyethyl)pyrazol, 2,3-diamino-dihydroxypyrazolopyrazolone dimethosulfonate, 4,5-diamino-1-hexylpyrazol, 2,3-diamino-6,7-dihydro-1H, 5H-pyrazolo[1,2-a]pyrazol-1-one, hydroxypropyl-p-phenylenediamine, dimethylpiperazinium aminopyrazolopyridine chloride hydrochloride, 4,5-diamino-3-methyl-1H-pyrazole-1-ethanol, 1-hexyl-3-methyl-1H-pyrazole-4,5-diamine, methylimidazolium-propyl p-phenylenediamine, hydroxyethoxy aminopyrazolopyridine, 2-(2,5-diaminophenyl)ethanol, N,N-bis-(2-hydroxyethyl)-p-phenylenediamine and addition salts, solvates and/or solvates of salts thereof, and any combination thereof.

11. The method for coloring hair according to claim 8 wherein each of the alkalizing agent and the source of carbonate/bicarbonate is present in a range of from about 0.1 wt % to about 10.0 wt % and the selected amino acid is present in an amount of from about 0.01 wt % to about 15.0 wt %, and wherein the wt %'s are relative to the total weight of the oxidative hair coloring composition.

12. The method for coloring hair according to claim 8 wherein the tint composition further comprises one or more of components J, K and L wherein:

component J comprises dicetyl phosphate, ceteth-10 phosphate and steareth-2 to 200;

component K comprises one or more of a C8-C20 fatty alcohol;

component L comprises at least one of ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), methylglycinediacetic acid (MGDA), tetrasodium glutamate diacetate (GLDA) salts, derivatives, and/or any combination thereof.

13. The method for coloring hair according to claim 8 wherein the oxidative hair coloring composition has a pH of from about 9 to about 10.

14. A kit for forming an oxidative hair coloring composition comprising:

A. a tint composition component comprising a cosmetically acceptable basic medium, an optional alkalizer, an L* mixture of a source of carbonate/bicarbonate, a source of ammonium cation and an amino acid selected from glycine; a precursor of at least MBB and a coupler of at least Aminol; and, B. an oxidizer composition component comprising at least a cosmetically acceptable acidic medium, hydrogen peroxide, a fatty alcohol, an anionic surfactant and a buffered acid to maintain an acidic pH of the oxidizer composition;

wherein the tint composition component and the oxidizer composition component are maintained separately and are free of resorcinol and C1-C10 alkyl resorcinol and halo resorcinol.

15. The kit according to claim 14 wherein the tint composition component further comprises: one or more of components J, K and L wherein:

component J comprises dicetyl phosphate, ceteth-10 phosphate and steareth-2 to 200;

component K comprises one or more of a C8-C20 fatty alcohol component L comprises at least one of ethylenediamine tetraacetic acid (EDTA), ethylenediamine-N,N'-disuccinic acid (EDDS), diethylenetriamine pentamethylene phosphonate (DTPMP), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), dimethyl glucamine (DMG), methylglycinediacetic acid (MGDA), tetrasodium glutamate diacetate (GLDA) salts, derivatives, and/or any combination thereof.

16. The kit according to claim 14 wherein the tint composition component further comprises: one or more of a secondary precursor and a secondary coupler wherein the secondary precursor comprises at least p-aminophenol (PAP), its addition salts, its solvates and/or solvates of its salts; and the secondary coupler comprises at least one or more of 2,4-diaminophenoxyethanol (DPE), its addition salts, its solvates and/or solvates of its salts, m-aminophenol (MAP), its addition salts, its solvates and/or solvates of its salts, 4-amino-2-hydroxy toluene (AHT), its addition salts, its solvates and/or solvates of its salts; and ethyl ortho-amino phenol (EOAP), its addition salts, its solvates and/or solvates of its salts.

17. The method according to claim 1 wherein the pseudo-resorcinol control manages color progression in the negative direction along the L* axis so as to reach a substantially constant level during a period of from about 20 to about 30 minutes.

* * * * *